(12) United States Patent
Kirsch et al.

(10) Patent No.: US 6,630,210 B2
(45) Date of Patent: Oct. 7, 2003

(54) PENTAFLUOROSULFURANYLBENZENE DERIVATIVES

(75) Inventors: Peer Kirsch, Darmstadt (DE); Joachim Krause, Dieburg (DE); Michael Heckmeier, Bensheim (DE)

(73) Assignee: Merck GmbH, Darmstadt (DE)

( * ) Notice: Subject to any disclaimer, the term of this patent is extended or adjusted under 35 U.S.C. 154(b) by 71 days.

(21) Appl. No.: 09/891,527

(22) Filed: Jun. 27, 2001

(65) Prior Publication Data

US 2002/0028306 A1 Mar. 7, 2002

(30) Foreign Application Priority Data

Jun. 28, 2000 (DE) .......................... 100 31 383

(51) Int. Cl.[7] .................. C09K 19/32; C09K 19/30; C09K 19/34; C09K 19/12; C07C 323/09; C07C 323/18; C07C 381/00; C07C 313/16; C07D 319/06
(52) U.S. Cl. ............. 428/1.1; 252/299.61; 252/299.62; 252/299.63; 252/299.66; 549/369; 568/74; 568/77; 570/129; 570/131
(58) Field of Search ...................... 428/1.1; 252/299.61, 252/299.62, 299.63, 299.66; 570/129, 131; 549/369; 568/74, 77

(56) References Cited

FOREIGN PATENT DOCUMENTS

| DE | 19748109 | * | 5/1999 |
|----|----------|---|--------|
| DE | 19933175 | * | 1/2000 |
| DE | 10058472 | * | 6/2001 |
| DE | 10124481 | * | 1/2002 |

OTHER PUBLICATIONS

Kirsch et al. (Angewandte Chemie, international Edition (2001, 40 (8), 180–1484), 2001.*

Caplus 2002: 568102.*

Caplus 2002: 446024.*

* cited by examiner

*Primary Examiner*—Shean C. Wu
(74) *Attorney, Agent, or Firm*—Millen, White, Zalano & Branigan, P.C.

(57) ABSTRACT

The invention relates to pentafluorosulfuranylbenzene derivatives of the formula I

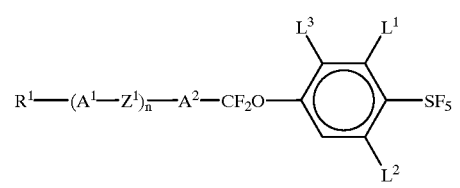

in which $R^1$, $A^1$, $A^2$, $Z^1$, $L^1$, $L^2$, $L^3$ and n are as defined herein and to the use thereof in liquid-crystalline media.

20 Claims, No Drawings

PENTAFLUOROSULFURANYLBENZENE DERIVATIVES

The invention includes novel pentafluorosulfuranylbenzene derivatives of the formula I

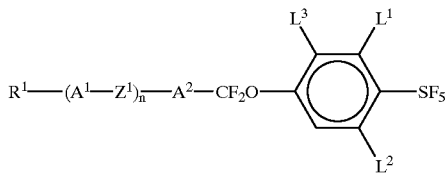

in which $R^1$ is H or an alkyl or alkylene radical having 1 to 15 carbon atoms which is unsubstituted or monosubstituted by CN or $CF_3$ or optionally monosubstituted to perhalo-substituted by halogen and in which, in addition, one or more non-adjacent $CH_2$ groups may each, independently of one another, be replaced by —O—, —S—, —CO—, C≡C—,

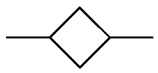

—CO—O—, —O—CO— or —O—CO—O— in such a way that oxygen atoms are not linked directly to one another, $A^1$ and $A^2$ are, independently of one another, a) a trans-cyclohexane-1,4-diyl radical, in which, in addition, one or more non-adjacent $CH_2$ groups may be replaced by —O— and/or —S—, b) a 1,4-phenylene radical, in which, in addition, one or two CH groups may be replaced by N, c) a radical selected from the group consisting of 1,4-bicyclo[2.2.2]-octylene, piperidine-1,4-diyl, naphthalene-2,6-diyl, decahydronaphthalene-2,6-diyl and 1,2,3,4-tetrahydronaphthalene-2,6-diyl, d) a cyclohexylene-1,4-diyl radical, where the radicals a), b), c) and d) may be substituted by CN, $CH_3$, Cl or F, $L^1$, $L^2$, $L^3$ are H, CN, F or Cl, $Z^1$ is —CO—O—, —O—CO—, —$CH_2$O—, —O—, —O$CH_2$—, —$CH_2CH_2$—, —CHF$CH_2$—, —CH=CH—, —$CH_2CF_2$—, —$CF_2CH_2$—, —$CF_2$—CHF—, —CHF$CF_2$—, —C≡C—, —$C_2F_4$—, —CF=CF—, —$OCF_2$—, —$CF_2$O— or a single bond, and n is 0, 1, 2 or 3.

The invention furthermore includes the use of these compounds as components of liquid-crystalline media, and to liquid-crystal and electro-optical display elements which contain the liquid-crystalline media according to the invention.

The compounds of the formula I can be used as components of liquid-crystalline media, in particular for displays based on the principle of the twisted cell, the guest-host effect, the effect of deformation of aligned phases (DAP) or electrically controlled birefringence (ECB) or the effect of dynamic scattering. The substances employed hitherto for this purpose all have certain disadvantages, for example inadequate stability to exposure to heat, light or electric fields, or unfavorable elastic and/or dielectric properties.

It has now been found that the compounds of the formula I are very suitable as components of liquid-crystalline media. They can be used to obtain stable liquid-crystalline media, in particular suitable for TFT or STN displays. The novel compounds of the formula I are notable for having a high clearing point in combination with relatively high Δ∈ values at the same time as broad nematic phases.

Generally, the provision of compounds of the formula I considerably broadens the range of liquid-crystalline substances which are suitable, from various applicational points of view, for the preparation of liquid-crystalline mixtures.

The compounds of the formula I have a broad range of applications. Depending on the choice of substituents, these compounds can serve as base materials of which liquid-crystalline media are predominantly composed; however, it is also possible to add compounds of the formula I to liquid-crystalline base materials from other classes of compounds in order, for example, to modify the dielectric and/or optical anisotropy of a dielectric of this type and/or to optimize its threshold voltage and/or its viscosity. The formula I furthermore encompasses all isotopes of the elements present in compounds of the formula I.

In the pure state, the compounds of the formula I are colorless and form liquid-crystalline mesophases in a temperature range which is favorably located for electro-optical use. They are stable chemically, thermally and to light.

The invention thus also includes the compounds of the formula I and use of these compounds as components of liquid-crystalline media. The invention furthermore includes liquid-crystalline media comprising at least one compound of the formula I, and to liquid-crystal display elements, in particular electro-optical display elements, which contain media of this type.

Hereinbefore and hereinafter, $R^1$, $A^1$, $A^2$, $Z^1$, $L^1$, $L^2$, $L^3$ and n are as defined above, unless expressly stated otherwise.

For simplicity, hereinafter $A^3$ is

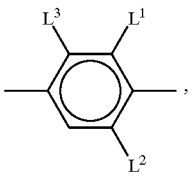

Cyc is a 1,4-cyclohexylene radical, Che is a 1,4-cyclohexenylene radical, Dio is a 1,3-dioxane-2,5-diyl radical, Dit is a 1,3-dithiane-2,5-diyl radical, Phe is a 1,4-phenylene radical, Pyd is a pyridine-2,5-diyl radical, Pyr is a pyrimidine-2,5-diyl radical, Bco is a bicyclo[2.2.2]-octylene radical, and Dec is a decahydronaphthalene radical, where Cyc and Phe may be unsubstituted or mono- or polysubstituted by $CH_3$, Cl, F or CN.

The formula I encompasses the preferred compounds Ia to Ic having two or three rings, respectively:

| | |
|---|---|
| $R^1$-$A^2$-$CF_2$O-$A^3$-$SF_5$ | Ia |
| $R^1$-$A^1$-$A^2$-$CF_2$O-$A^3$-$SF_5$ | Ib |
| $R^1$-$A^1$-$Z^1$-$A^2$-$CF_2$O-$A^3$-$SF_5$ | Ic | in which $R^1$, $A^1$, $A^2$, $A^3$ and $Z^1$ are as defined above.

$R^1$ is preferably straight-chain alkyl or alkoxy having 1 to 10 carbon atoms or alkenyl or alkenyloxy having 2 to 10 carbon atoms. n is preferably 1 or 2.

$A^1$ is preferably Phe, Cyc, Che, Pyd, Pyr or Dio, in particular Phe, Cyc or Dio. The compounds of the formula I preferably comprise not more than one of the radicals Bco, Dec, Pyd, Pyr or Dit.

The cyclohexene-1,4-diyl group is preferably of the following structures:

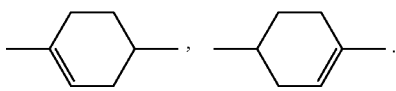

If the radical $A^1$ (n=2 or 3) occurs more than once, the two rings can have the same or different meanings. The same applies to the bridge $Z^1$ and to all other groups which occur more than once in the compounds of the formula I.

$A^1$ is preferably trans-cyclohexane-1,4-diyl or 1,4-phenylene.

Preference is likewise given to compounds of the formula I and all sub-formulae in which $A^1$ and/or $A^2$ are/is 1,4-phenylene which is mono- or disubstituted by F or CN.

$A^1$ and $A^2$ are preferably, independently of one another,

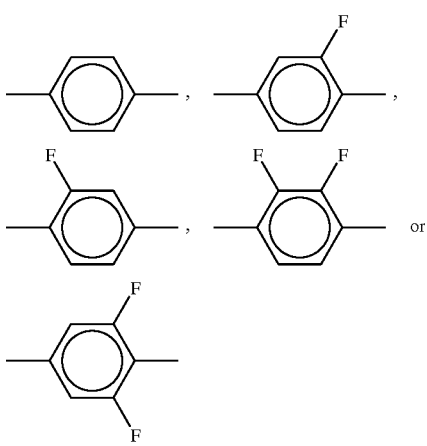

$Z^1$ is preferably —CH$_2$CH$_2$—, —CH=CH—, —C≡C—, —CF$_2$CF$_2$—, —CF=CF—, —CF$_2$O—, —OCF$_2$— or a single bond, in particular a single bond, —CH$_2$CH$_2$— or —CF$_2$CF$_2$—.

Preference is given to compounds of the formula I which are characterized in that $R^1$ is straight-chain alkyl or alkoxy having 1 to 10 carbon atoms or alkenyl having 2 to 10 carbon atoms and Z is —CF$_2$CF$_2$— or —CF=CF—.

Compounds of the formula I in which $A^2$ is

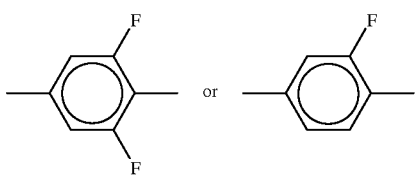

represent a preferred embodiment of the invention.

Particular preference is given to those compounds of the formula I which are characterized in that $R^1$ is straight-chain alkyl or alkenyloxy having 1 to 10 carbon atoms or alkenyl or alkenyloxy having 2 to 10 carbon atoms and $A^1$ is

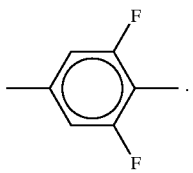

The following group of compounds of the sub-formulae I1 to I71 represents another preferred embodiment of the invention.

I1
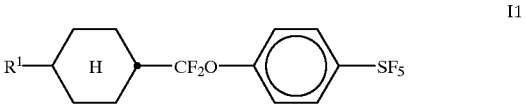

I2
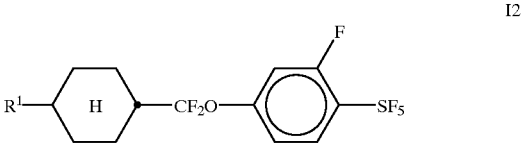

I3
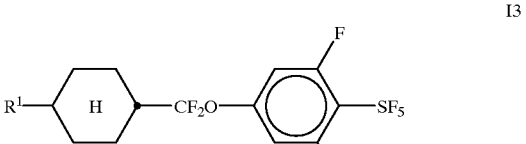

I4
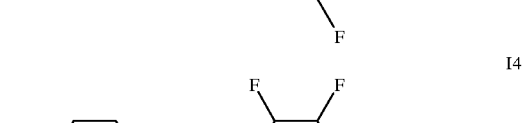

I5
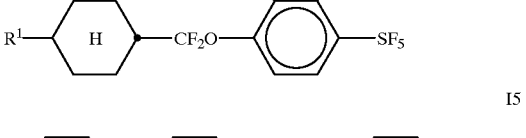

I6
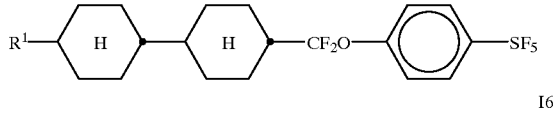

I7
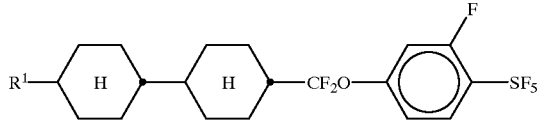

I8
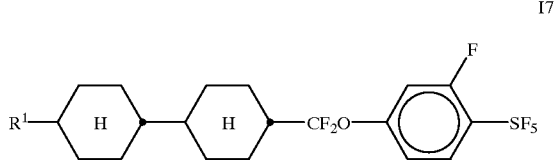

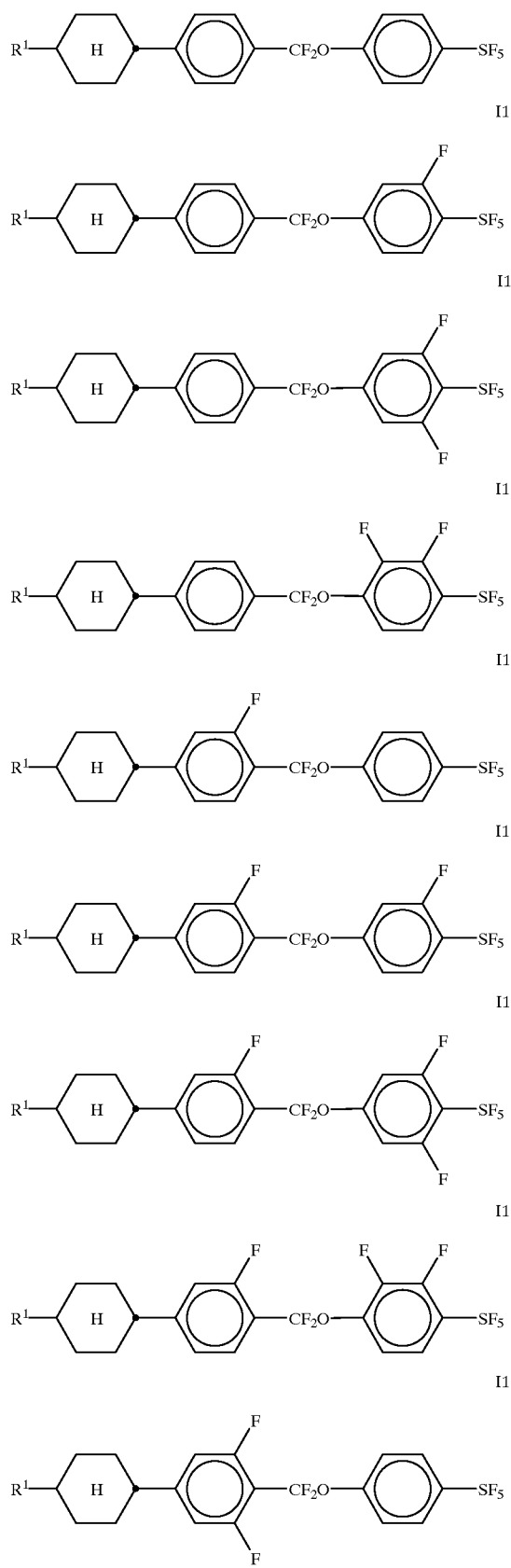
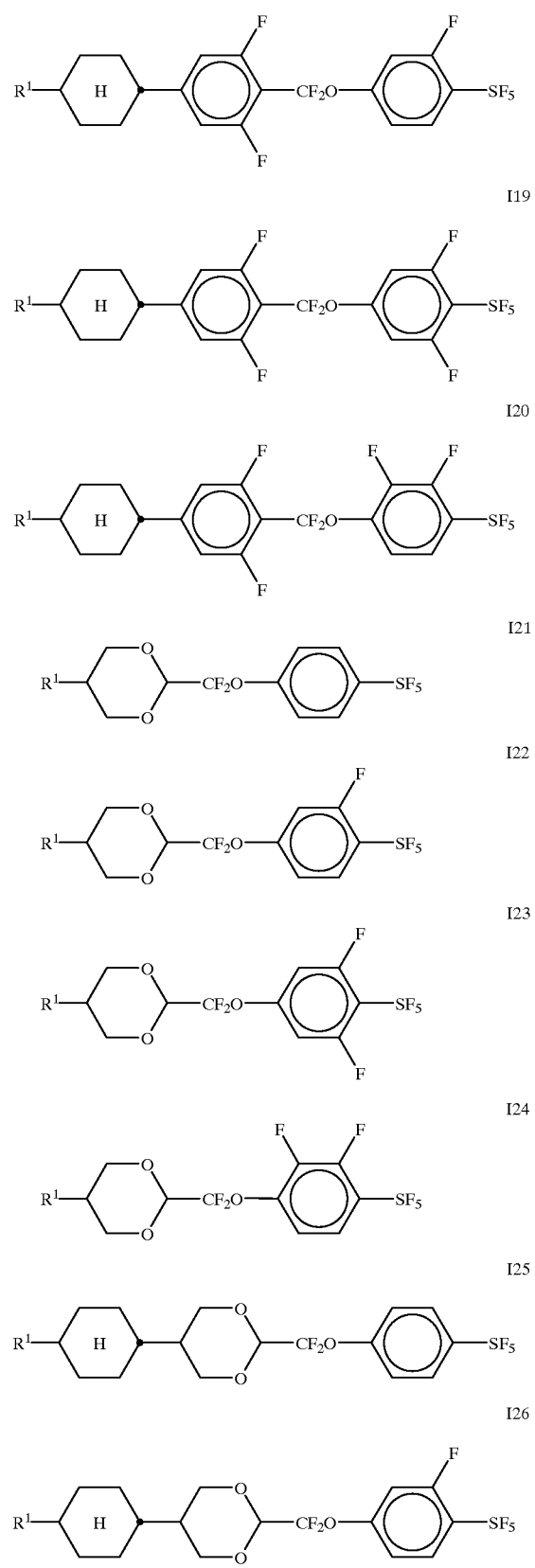

I27
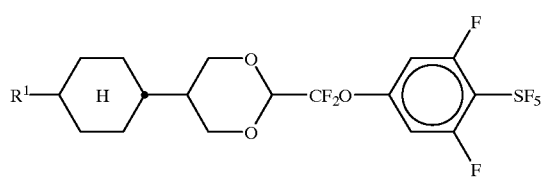
I28
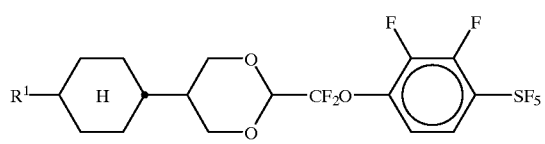
I29
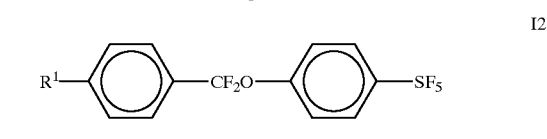
I30
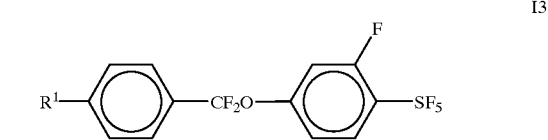
I31
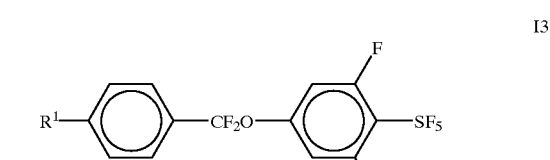
I32
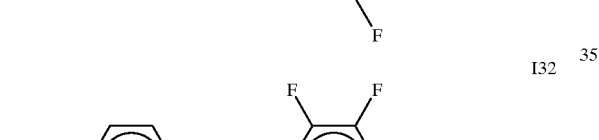
I33
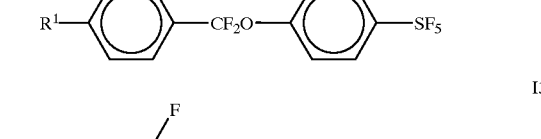
I34
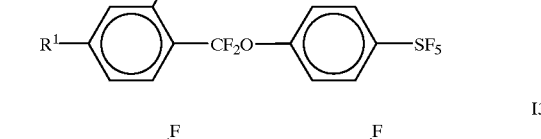
I35
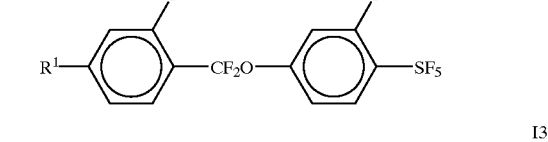
I36
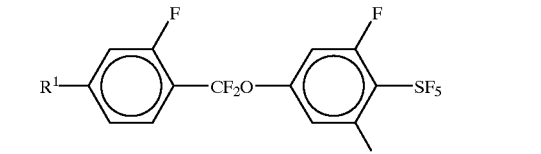
I37
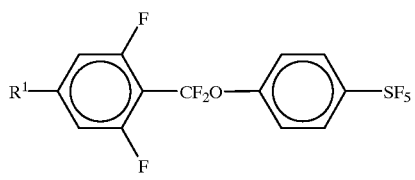
I38
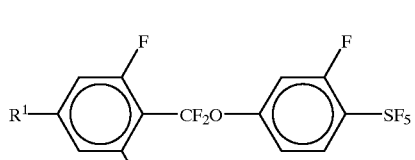
I39
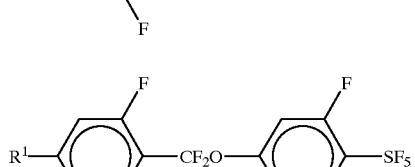
I40
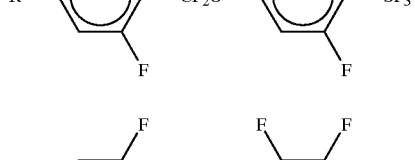
I41
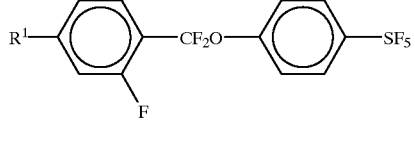
I42
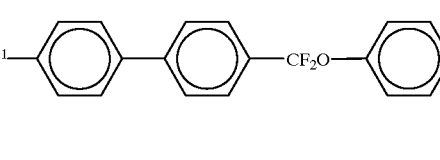
I43
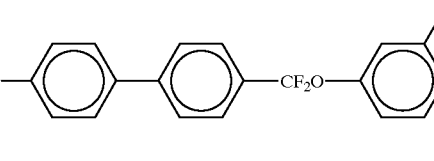
I44
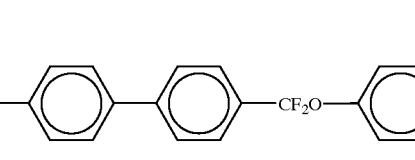
I45
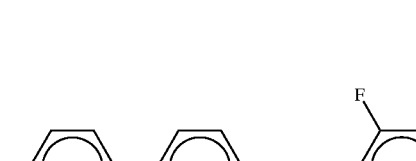

-continued

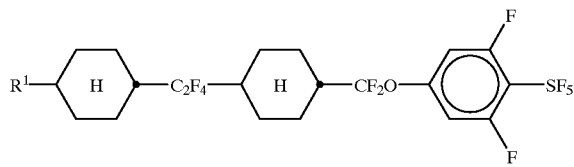
I63

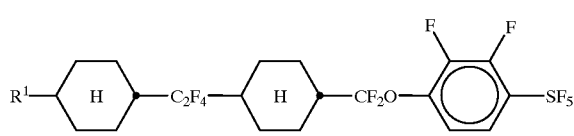
I64

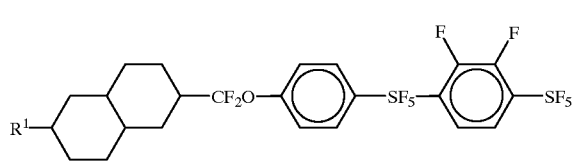
I65

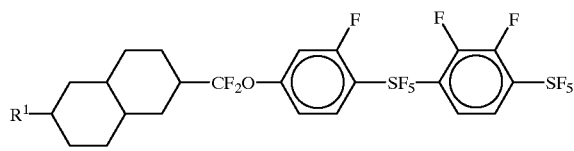
I66

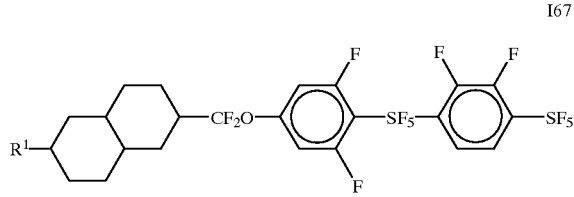
I67

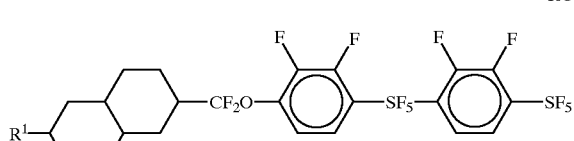
I68

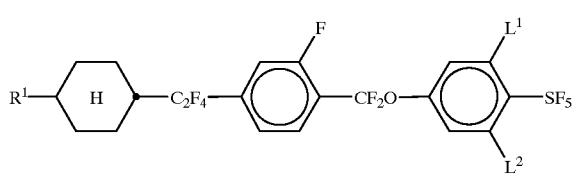
I70

-continued

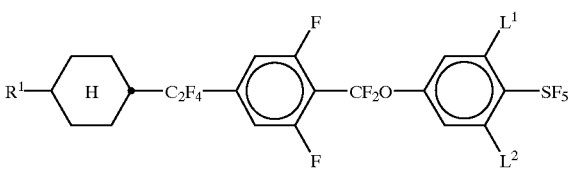
I71 in which $R^1$ is as defined above.

If $R^1$ in the formulae above and below is an alkyl and/or alkoxy radical, this can be straight-chain or branched. It is preferably straight-chain, has 2, 3, 4, 5, 6 or 7 carbon atoms and accordingly is preferably ethyl, propyl, butyl, pentyl, hexyl, heptyl, ethoxy, propoxy, butoxy, pentyloxy, hexyloxy or heptyloxy, furthermore methyl, octyl, nonyl, decyl, undecyl, dodecyl, tridecyl, tetradecyl, pentadecyl, methoxy, octyloxy, nonyloxy, decyloxy, undecyloxy, dodecyloxy, tridecyloxy or tetradecyloxy.

Oxaalkyl is preferably straight-chain 2-oxapropyl (=methoxymethyl), 2-(=ethoxymethyl) or 3-oxabutyl (=2-methoxyethyl), 2-, 3- or 4-oxapentyl, 2-, 3-, 4- or 5-oxahexyl, 2-, 3-, 4-, 5- or 6-oxaheptyl, 2-, 3-, 4-, 5-, 6- or 7-oxaoctyl, 2-, 3-, 4-, 5-, 6-, 7- or 8-oxanonyl, or 2-, 3-, 4-, 5-, 6-, 7-, 8- or 9-oxadecyl.

If $R^1$ is an alkyl radical in which one $CH_2$ group has been replaced by —CH=CH—, this can be straight-chain or branched. It is preferably straight-chain and has 2 to 10 carbon atoms. Accordingly, it is in particular vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl, oct-1-, -2-, -3-, -4-, -5-, -6- or -7-enyl, non-1-, -2-, -3-, -4-, -5-, -6-, -7- or -8-enyl, or dec-1-, -2-, -3-, -4-, -5-, -6-, -7-, -8- or -9-enyl.

If $R^1$ is an alkyl radical in which one $CH_2$ group has been replaced by —O— and one has been replaced by —CO—, these are preferably adjacent. These thus contain an acyloxy group —CO—O— or an oxycarbonyl group —O—CO—. These are preferably straight-chain and have 2 to 6 carbon atoms.

Accordingly, they are in particular acetoxy, propionyloxy, butyryloxy, pentanoyloxy, hexanoyloxy, acetoxymethyl, propionyloxymethyl, butyryloxymethyl, pentanoyloxymethyl, 2-acetoxyethyl, 2-propionyloxyethyl, 2-butyryloxyethyl, 3-acetoxypropyl, 3-propionyloxypropyl, 4-acetoxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl or 4-(methoxycarbonyl)butyl.

If $R^1$ is an alkyl radical in which one $CH_2$ group has been replaced by unsubstituted or substituted —CH=CH— and an adjacent $CH_2$ group has been replaced by CO or CO—O— or O—CO, this can be straight-chain or branched. It is preferably straight-chain and has 4 to 13 carbon atoms. Accordingly, it is in particular acryloyloxymethyl, 2-acryloyloxyethyl, 3-acryloyloxypropyl, 4-acryloyloxybutyl, 5-acryloyloxypentyl, 6-acryloyloxyhexyl, 7-acryloyloxyheptyl, 8-acryloyloxyoctyl, 9-acryloyloxynonyl, 10-acryloyloxydecyl, methacryloyloxymethyl, 2-methacryloyloxyethyl, 3-methacryloyloxypropyl, 4-methacryloyloxybutyl, 5-methacryloyloxypentyl, 6-methacryloyloxyhexyl, 7-methacryloyloxyheptyl, 8-methacryloyloxyoctyl or 9-methacryloyloxynonyl.

If $R^1$ is an alkyl or alkenyl radical which is monosubstituted by CN or $CF_3$, this radical is preferably straight-chain and the substitution by CN or $CF_3$ is preferably in ω-position.

If $R^1$ is an alkyl or alkenyl radical which is at least monosubstituted by halogen, this radical is preferably straight-chain and halogen is preferably F or Cl. In the case of polysubstitution, halogen is preferably F. The resulting radicals also include perfluorinated radicals. In the case of monosubstitution, the fluoro or chloro substituent can be in any desired position, but is preferably in the ω-position.

Compounds of the formula I containing branched pendant groups $R^1$ may occasionally be of importance owing to better solubility in the conventional liquid-crystalline base materials, but in particular as chiral dopants if they are optically active. Smectic compounds of this type are suitable as components for ferro-electric materials.

Branched groups of this type generally contain not more than one chain branch. Preferred branched radicals $R^1$ are isopropyl, 2-butyl (=1-methylpropyl), isobutyl (=2-methylpropyl), 2-methylbutyl, isopentyl (=3-methylbutyl), 2-methylpentyl, 3-methylpentyl, 2-ethylhexyl, 2-propylpentyl, isopropoxy, 2-methylpropoxy, 2-methylbutoxy, 3-methylbutoxy, 2-methylpentoxy, 3-methylpentoxy, 2-ethylhexoxy, 1-methylhexoxy or 1-methylheptoxy.

The formula I encompasses both the racemates of these compounds and the optical antipodes, and mixtures thereof.

Of these compounds of the formula I and the sub-formulae, preference is given to those in which at least one of the radicals present therein has one of the preferred meanings indicated.

In the compounds of the formula I, preference is given to those stereoisomers in which the rings Cyc and piperidine are trans-1,4-disubstituted. Those of the abovementioned formulae which contain one or more groups Pyd, Pyr and/or Dio encompass in each case the two 2,5-positional isomers.

The compounds of the formula I are prepared by methods known per se, as described in the literature (for example in the standard works, such as Houben-Weyl, Methoden der Organischen Chemie, Georg-Thieme-Verlag, Stuttgart), to be precise under reaction conditions which are known and suitable for said reactions.

Use can also be made here of variants which are known per se, but are not mentioned here in greater detail.

The compounds according to the invention can be prepared, for example, as shown in the following reaction schemes:

Scheme 1

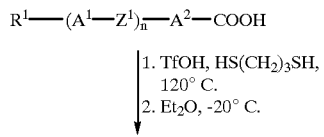

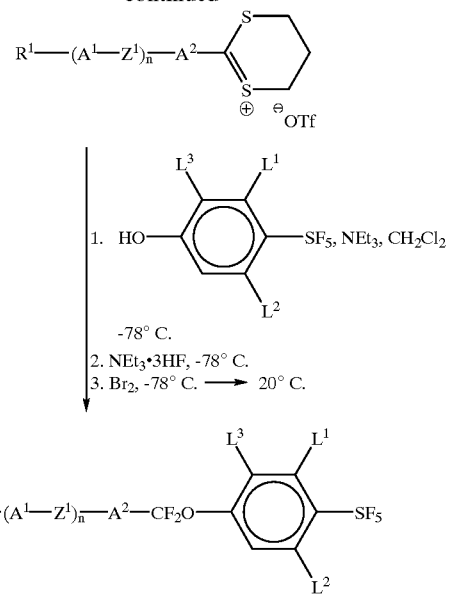

The synthesis of 4-pentafluorosulfuranylphenol is known, for example, from W. A. Sheppard, J. Am. Chem. Soc. 1962, 84, 3072–3076, or P. Kirsch et al., Angew. Chem. 1999, 111, 2174–2178.

Esters of the formula I can also be obtained by esterification of corresponding carboxylic acids (or reactive derivatives thereof) using alcohols or phenols (or reactive derivatives thereof) or by the DCC method (DCC=dicyclohexylcarbodiimide).

The corresponding carboxylic acids and alcohols or phenols are known or can be prepared analogously to known processes.

Suitable reactive derivatives of said carboxylic acids are in particular the acid halides, especially the chlorides and bromides, furthermore the anhydrides, azides or esters, in particular alkyl esters having 1–4 carbon atoms in the alkyl group.

Suitable reactive derivatives of said alcohols or phenols are in particular the corresponding metal alkoxides or phenoxides, preferably of an alkali metal, such as Na or K.

The esterification is advantageously carried out in the presence of an inert solvent. Particularly suitable solvents are ethers, such as diethyl ether, di-n-butyl ether, THF, dioxane or anisole, ketones, such as acetone, butanone or cyclohexanone, amides, such as DMF or hexamethylphosphoric triamide, hydrocarbons, such as benzene, toluene or xylene, halogenated hydrocarbons, such as tetrachloromethane or tetrachloroethylene, and sulfoxides, such as dimethyl sulfoxide or sulfolane. Water-immiscible solvents can at the same time advantageously be used for removal by azeotropic distillation of the water formed during the esterification. It may in some cases also be possible to use an excess of an organic base, for example pyridine, quinoline or triethylamine, as solvent for the esterification. The esterification can also be carried out in the absence of a solvent, for example by simply heating the components in the presence of sodium acetate. The reaction temperature is usually between –50° C. and +250° C., preferably between –20° C. and +80° C. At these temperatures, the esterification reactions are generally complete after from 15 minutes to 48 hours.

Specifically, the reaction conditions for the esterification depend substantially on the nature of the starting materials used. Thus, the reaction of a free carboxylic acid with a free alcohol or phenol is generally carried out in the presence of a strong acid, for example a mineral acid, such as hydrochloric acid or sulphuric acid. A preferred reaction procedure is to react an acid anhydride or, in particular, an acid chloride with an alcohol, preferably in a basic medium, important bases being, in particular, alkali metal hydroxides, such as sodium hydroxide or potassium hydroxide, alkali metal carbonates or hydrogencarbonates, such as sodium carbonate, sodium hydrogencarbonate, potassium carbonate or potassium hydrogencarbonate, alkali metal acetates, such as sodium acetate or potassium acetate, alkaline earth metal hydroxides, such as calcium hydroxide, or organic bases, such as triethylamine, pyridine, lutidine, collidine or quinoline. A further preferred embodiment of the esterification comprises first converting the alcohol or phenol into the sodium or potassium alkoxide or phenoxide, for example by treatment with ethanolic sodium hydroxide or potassium hydroxide solution, and isolating the product and reacting it with an acid anhydride or, in particular, acid chloride.

Nitriles can be obtained by halogen substitution using copper cyanide or alkali metal cyanide.

In a further process for the preparation of compounds of the formula I in which $Z^1$ is —CH=CH—, an aryl halide is reacted with an olefin in the presence of a tertiary amine and in the presence of a palladium catalyst (cf. R. F. Heck, Acc. Chem. Res. 12 (1979) 146). Examples of suitable aryl halides are chlorides, bromides and iodides, in particular bromides and iodides. The tertiary amines necessary for the success of the coupling reaction, such as, for example, triethylamine, are also suitable as solvent. Examples of suitable palladium catalysts are its salts, in particular Pd(II) acetate, with organophosphorus(III) compounds, such as, for example, triarylphosphines. This process can be carried out in the presence or absence of an inert solvent at temperatures between about 0° C. and 150° C., preferably between 20° C. and 100° C.; suitable solvents are, for example, nitriles, such as acetonitrile, or hydrocarbons, such as benzene or toluene. The aryl halides and olefins employed as starting materials are frequently commercially available and can be prepared by processes known from the literature, for example by halogenation of corresponding parent compounds or by elimination reactions using corresponding alcohols or halides.

In this manner, it is, for example, possible to prepare stilbene derivatives. The stilbenes can furthermore be prepared by reaction of a 4-substituted benzaldehyde with a corresponding phosphorus ylide, according to Wittig. However, it is also possible to prepare tolans of the formula I by using monosubstituted acetylene instead of the olefin (Synthesis 627 (1980) or Tetrahedron Lett. 27, 1171 (1986)).

Furthermore, aromatics can be coupled by reacting aryl halides with aryltin compounds. These reactions are preferably carried out with the addition of a catalyst, such as, for example, a palladium(0) complex, in inert solvents, such as hydrocarbons, at elevated temperatures, for example in boiling xylene, under an inert gas.

Coupling reactions of alkynyl compounds with aryl halides can be carried out analogously to the process described by A. O. King, E. Negishi, F. J. Villani and A. Silveira in J. Org. Chem. 43, 358 (1978).

Tolans of the formula I in which $Z^1$ is —C≡C— can also be prepared via the Fritsch-Buttenberg-Wiechell rearrangement (Ann. 279, 319, 1984), in which 1,1-diaryl-2-haloethylenes are rearranged to diarylacetylenes in the presence of strong bases.

Tolans of the formula I can also be prepared by brominating the corresponding stilbenes and then subjecting the product to dehydrohalogenation. It is possible to use variations known per se of this reaction not mentioned here in more detail.

Ethers of the formula I can be obtained by etherification of the corresponding hydroxy compounds, preferably of the corresponding phenols, in which the hydroxy compound is preferably first converted to the corresponding metal derivative, for example by treatment with NaH, NaNH$_2$, NaOH, KOH, Na$_2$CO$_3$ or K$_2$CO$_3$ to the corresponding alkali metal alcoxide or alkali metal phenoxide. This derivative can then be reacted with the corresponding alkyl halide, alkyl sulfonate or dialkyl sulfate, preferably in an inert solvent, such as, for example, acetone, 1,2-dimethoxyethane, DMF or dimethyl sulfoxide or even with excess aqueous or aqueous-alcoholic NaOH or KOH at temperatures between about 20° C. and 100° C.

In order to prepare the laterally substituted fluorine or chlorine compounds of the formula I, corresponding aniline derivatives can be reacted with sodium nitrite and either with tetrafluoroboric acid (in order to introduce an F atom) or with copper(I) chloride (in order to introduce a chlorine atom), to give the diazonium salts, which are then decomposed thermally at temperatures of 100–140° C.

Linking of an aromatic nucleus to a nonaromatic nucleus or of two aromatic nuclei is preferably obtained by condensation of an organolithium or organomagnesium compound with a ketone, if an aliphatic group $Z^1$ is intended to be located between the nuclei.

The origanometallic compounds are prepared, for example, by metal-halogen exchange (for example in accordance with Org. React. 6, 339–366 (1951)) between the corresponding halogen compound and an organolithium compound, preferably, tert-butyllithium or lithium naphthalenide, or by reaction with magnesium turnings.

Two aromatic rings are preferably linked to an aromatic ring by Friedel-Crafts alkylation or acylation by reacting the corresponding aromatic compounds in the presence of a Lewis acid catalyst. Examples of suitable Lewis acids are SnCl$_4$, ZnCl$_2$, AlCl$_3$ and TiCl$_4$.

Two aromatic rings can furthermore be linked by Ullmann reaction (for example Synthesis 1974, p. 9) between aryl iodides and copper iodide, but preferably between an aryl-copper compound and an aryl iodide, or by the Gomberg-Bachmann reaction between an aryl diazonium salt and the corresponding aromatic compound (for example Org. React. 2, 224 (1944)).

The tolans of the formula I ($Z^1$=—C≡C—) are prepared, for example, by reacting the corresponding aryl halides with an acetylide in a basic solvent in the presence of a transition metal catalyst; palladium catalysts can preferably be used here, in particular a mixture of bis(triphenylphosphine) palladium(II) chloride and copper iodide in piperidine as solvent.

Furthermore, the compounds of the formula I can be prepared by reducing a compound which contains one or more reducible groups and/or C—C bonds in place of H atoms, but otherwise corresponds to the formula I.

Suitable reducible groups are preferably carbonyl groups, in particular keto groups, furthermore, for example, free or esterified hydroxyl groups or aromatically bonded halogen atoms. Preferred starting materials for the reduction are compounds which conform to the formula I, but contain a cyclohexene ring or cyclohexanone ring in place of a cyclohexane ring and/or contain a —CH=CH— group in place of a —CH$_2$CH$_2$— group and/or contain a —CO— group in place of a —CH$_2$— group and/or contain a free or functionally modified (for example in the form of its p-toluenesulfonate) OH group in place of an hydrogen atom.

The reduction can be carried out, for example, by catalytic hydrogenation at temperatures between about 0° C. and about 200° C. and at pressures between about 1 and 200 bar in an inert solvent, for example an alcohol, such as methanol, ethanol or isopropanol, an ether, such as tetrahydrofuran (THF) or dioxane, an ester, such as ethyl acetate, a carboxylic acid, such as acetic acid, or a hydrocarbon, such as cyclohexane. Suitable catalysts are expediently noble metals, such as Pt or Pd, which may be employed in the form of oxides (for example $PtO_2$ or PdO), on a support (for example Pd on charcoal, calcium carbonate or strontium carbonate) or in finely divided form.

Ketones can also be reduced by the methods of Clemmensen (using zinc, zinc amalgam or tin and hydrochloric acid, expediently in aqueous-alcoholic solution or in the heterogeneous phase with water/toluene at temperatures between about 80 and 120° C.) or Wolff-Kishner (using hydrazine, expediently in the presence of alkali, such as KOH or NaOH, in a high-boiling solvent, such as diethylene glycol or triethylene glycol, at temperatures between about 100 and 200° C.) to give the corresponding compounds of the formula I which contain alkyl groups and/or —$CH_2CH_2$— bridges.

Furthermore, reductions using complex hydrides are possible. For example, arylsulfonyloxy groups can be removed reductively using $LiAlH_4$, in particular p-toluenesulfonyloxymethyl groups can be reduced to methyl groups, expediently in an inert solvent such as diethyl ether or THF at temperatures between about 0 and 100° C. Double bonds can be hydrogenated using $NaBH_4$ or tributyltin hydride in methanol.

The starting materials are either known or can be prepared analogously to known compounds.

The liquid-crystalline media according to the invention preferably comprise from 2 to 40 components, in particular from 4 to 30 components, as further constituents besides one or more compounds according to the invention. These media very particularly preferably comprise from 7 to 25 components besides one or more compounds according to the invention. These further constituents are preferably selected from nematic or nematogenic (monotropic or isotropic) substances, in particular substances from the classes of the azoxybenzenes, benzylideneanilines, biphenyls, terphenyls, phenyl or cyclohexyl benzoates, phenyl or cyclohexyl cyclohexanecarboxylates, phenyl or cyclohexyl cyclohexylbenzoates, phenyl or cyclohexyl cyclohexylcyclohexanecarboxylates, cyclohexylphenyl benzoates, cyclohexanecarboxylates and cyclohexylcyclohexanecarboxylates, phenylcyclohexanes, cyclohexylbiphenyls, phenylcyclohexylcyclohexanes, cyclohexylcyclohexanes, cyclohexylcyclohexylcyclohexenes, 1,4-bis-cyclohexylbenzenes, 4,4'-bis-cyclohexylbiphenyls, phenyl- or cyclohexylpyrimidines, phenyl- or cyclohexylpyridines, phenyl- or cyclohexyldioxanes, phenyl- or cyclohexyl-1,3-dithianes, 1,2-diphenylethanes, 1,2-dicyclohexylethanes, 1-phenyl-2-cyclohexylethanes, 1-cyclohexyl-2-(4-phenylcyclohexyl)ethanes, 1-cyclohexyl-2-biphenylethanes, 1-phenyl-2-cyclohexylphenylethanes, optionally halogenated stilbenes, benzyl phenyl ethers, tolans and substituted cinnamic acids. The 1,4-phenylene groups in these compounds may also be fluorinated.

Particularly preferred compounds suitable as further constituents of media according to the invention can be characterized by the formulae 1, 2, 3, 4 and 5:

| | |
|---|---|
| R'-L-E-R" | 1 |
| R'-L-COO-E-R" | 2 |
| R'-L-OOC-E-R" | 3 |
| R'-L-$CH_2CH_2$-E-R" | 4 |
| R'-L-C≡C-E-R" | 5 |

In the formulae 1, 2, 3, 4 and 5, L and E, which may be identical or different, are in each case, independently of one another, a bivalent radical from the group formed by -Phe-, -Cyc-, -Phe-Phe-, -Phe-Cyc-, -Cyc-Cyc-, -Pyr-, -Dio-, -G-Phe- and -G-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl and G is 2-(trans-1,4-cyclohexyl)ethyl, pyrimidine-2,5-diyl, pyridine-2,5-diyl or 1,3-dioxane-2,5-diyl.

One of the radicals L and E is preferably Cyc, Phe or Pyr. E is preferably Cyc, Phe or Phe-Cyc. The media according to the invention preferably comprise one or more components selected from the compounds of the formulae 1, 2, 3, 4 and 5 in which L and E are selected from the group consisting of Cyc, Phe and Pyr and simultaneously one or more components selected from the compounds of the formulae 1, 2, 3, 4 and 5 in which one of the radicals L and E is selected from the group consisting of Cyc, Phe and Pyr and the other radical is selected from the group consisting of -Phe-Phe-, -Phe-Cyc-, -Cyc-Cyc-, -G-Phe- and -G-Cyc-, and optionally one or more components selected from the compounds of the formulae 1, 2, 3, 4 and 5 in which the radicals L and E are selected from the group consisting of -Phe-Cyc-, -Cyc-Cyc-, -G-Phe- and -G-Cyc-.

In a smaller subgroup of the compounds of the formulae 1, 2, 3, 4 and 5, R' and R" are each, independently of one another, alkyl, alkenyl, alkoxy, alkoxyalkyl, alkenyloxy or alkanoyloxy having up to 8 carbon atoms. This smaller subgroup is called group A below, and the compounds are denoted by the sub-formulae 1a, 2a, 3a, 4a and 5a. In most of these compounds, R' and R" are different from one another, one of these radicals usually being alkyl, alkenyl, alkoxy or alkoxyalkyl.

In another smaller subgroup of the compounds of the formulae 1, 2, 3, 4 and 5, which is called group B, R" is —F, —Cl, —NCS or —$(O)_iCH_{3-(k+1)}F_kCl_1$, where i is 0 or 1, and k and 1 are 1, 2 or 3; the compounds in which R" has this meaning are denoted by the sub-formulae 1b, 2b, 3b, 4b and 5b. Particular preference is given to those compounds of the sub-formulae 1b, 2b, 3b, 4b and 5b in which R" is —F, —Cl, —NCS, —$CF_3$, —$OCHF_2$ or —$OCF_3$.

In the compounds of the sub-formulae 1b, 2b, 3b, 4b and 5b, R' is as defined for the compounds of the sub-formulae 1a–5a and is preferably alkyl, alkenyl, alkoxy or alkoxyalkyl.

In a further smaller subgroup of the compounds of the formulae 1, 2, 3, 4 and 5, R" is —CN; this subgroup is called group C below, and the compounds of this sub-group are correspondingly described by sub-formulae 1c, 2c, 3c, 4c and 5c. In the compounds of the sub-formulae 1c, 2c, 3c, 4c and 5c, R' is as defined for the compounds of the sub-formulae 1a–5a and is preferably alkyl, alkoxy or alkenyl.

In addition to the preferred compounds of groups A, B and C, other compounds of the formulae 1, 2, 3, 4 and 5 having other variants of the proposed substituents are also customary. All these substances can be obtained by methods which are known from the literature or analogously thereto.

Besides compounds of the formula I according to the invention, the media according to the invention preferably comprise one or more compounds selected from group A and/or group B and/or group C. The proportions by weight of the compounds from these groups in the media according to the invention are preferably:

Group A: from 0 to 90%, preferably from 20 to 90%, in particular from 30 to 90%

Group B: from 0 to 80%, preferably from 10 to 80%, in particular from 10 to 65%

Group C: from 0 to 80%, preferably from 5 to 80%, in particular from 5 to 50%, the sum of the proportions by weight of the group A and/or B and/or C compounds present in the particular media according to the invention preferably being from 5 to 90% and in particular from 10 to 90%.

The media according to the invention preferably comprise from 1 to 40%, particularly preferably from 5 to 30%, of the compounds according to the invention. Preference is furthermore given to media which comprise more than 40%, in particular from 45 to 90%, of compounds according to the invention. The media preferably comprise one, two, three, four or five compounds according to the invention.

The construction of the STN or MLC display according to the invention from polarizers, electrode base plates and surface-treated electrodes corresponds to the conventional construction for displays of this type. The term conventional construction is broadly drawn here and also covers all variations and modifications of the MLC display, in particular including matrix display elements based on poly-Si TFT or MIM and especially reflective displays.

Optionally, a significant difference between the displays according to the invention and the hitherto conventional displays based on the twisted nematic cell consists in the choice of the liquid-crystal parameters of the liquid-crystal layer.

The liquid-crystal mixtures which can be used in accordance with the invention are prepared in a manner conventional per se. In general, the desired amount of the components used in a lesser amount is dissolved in the components making up the principal constituent, expediently at elevated temperature. It is also possible to mix solutions of the components in an organic solvent, for example in acetone, chloroform or methanol, and to remove the solvent again after thorough mixing, for example by distillation. It is also possible to prepare the mixtures in other conventional manners, for example by using pre-mixtures, for example homologue mixtures, or using so-called "multi-bottle" systems.

The dielectrics may also comprise further additives known to the person skilled in the art and described in the literature. For example, 0–15%, preferably 0–10%, of pleochroic dyes and/or chiral dopants can be added. The individual added compounds are each employed in concentrations of from 0.01 to 6%, preferably from 0.1 to 3%. However, the concentration data for the other constituents of the liquid-crystal mixtures, i.e. of the liquid-crystalline or mesogenic compounds, are given without taking into account the concentration of these additives.

In the foregoing and in the following examples, all temperatures are set froth uncorrected in degrees Celsius; and, unless otherwise indicated, all parts and percentages are by weight.

The entire disclosure of all applications, patents and publications, cited above and below, and of corresponding German application no. 10031383.3, filed Jun. 28, 2000 is hereby incorporated by reference.

EXAMPLES

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

C denotes a crystalline phase, S a smectic phase, $S_C$ a smectic C phase, N a nematic phase and I the isotropic phase.

In the present application and in the following examples, the structures of the liquid-crystal compounds are specified by acronyms, which are transformed into chemical formulae according to the following Tables A and B. All radicals $C_nH_{2n+1}$ and $C_mH_{2m+1}$ are straight-chain alkyl radicals having n or m C atoms; m and n are each an integer, preferably 1, 2, 3, 4, 5, 6, 7, 8, 9, 10, 11 or 12, where n=m or n≠m. The coding according to Table B is self-evident. Table A specifies the acronym for the parent body only. In individual cases, the acronym for the parent body is followed, separated therefrom by a hyphen, by a code for the substituents $R^{1*}$, $R^{2*}$, $L^{1*}$ and $L^{2*}$:

| Code for $R^{1*}$, $R^{2*}$, $L^{1*}$, $L^{2*}$ | $R^{1*}$ | $R^{2*}$ | $L^{1*}$ | $L^{2*}$ |
| --- | --- | --- | --- | --- |
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nF.F.F | $C_nH_{2n+1}$ | F | F | F |
| $nCF_3$ | $C_nH_{2n+1}$ | $CF_3$ | H | H |
| $nOCF_3$ | $C_nH_{2n+1}$ | $OCF_3$ | H | H |
| $nOCF_2$ | $C_nH_{2n+1}$ | $OCHF_2$ | H | H |
| nS | $C_nH_{2n+1}$ | NCS | H | H |
| rVsN | $C_rH_{2r+1}-CH=CH-C_sH_{2s}-$ | CN | H | H |
| V-T | $CH_2=CH$ | $CF_3$ | H | H |
| V2-T | $CH_2=CH-C_2H_4$ | $CF_3$ | H | H |
| 1V-OT | $CH_3-CH=CH$ | $OCF_3$ | H | H |
| rEsN | $C_rH_{2r+1}-O-C_sH_{2s}-$ | CN | H | H |
| nAm | $C_nH_{2n+1}$ | $COOC_mH_{2m+1}$ | H | H |
| $nOCCF_2.F.F$ | $C_nH_{2n+1}$ | $OCH_2CF_2H$ | F | F |

Preferred mixture components are shown in Tables A and B.
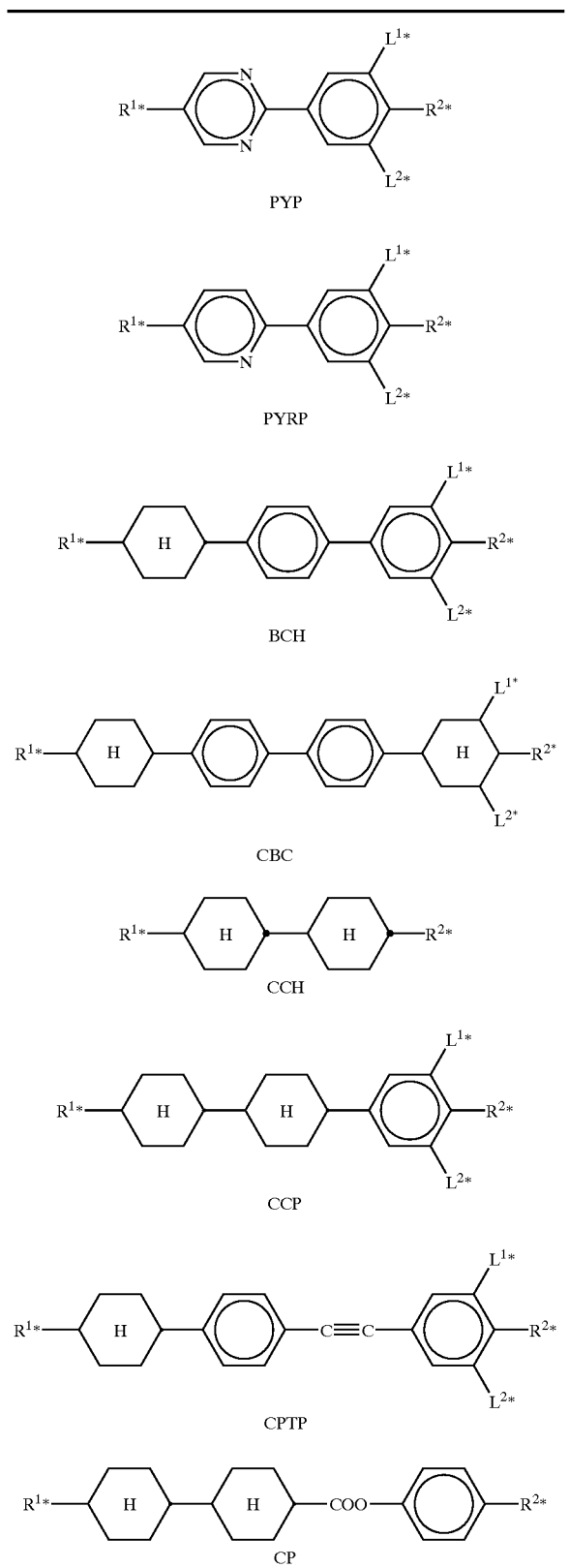
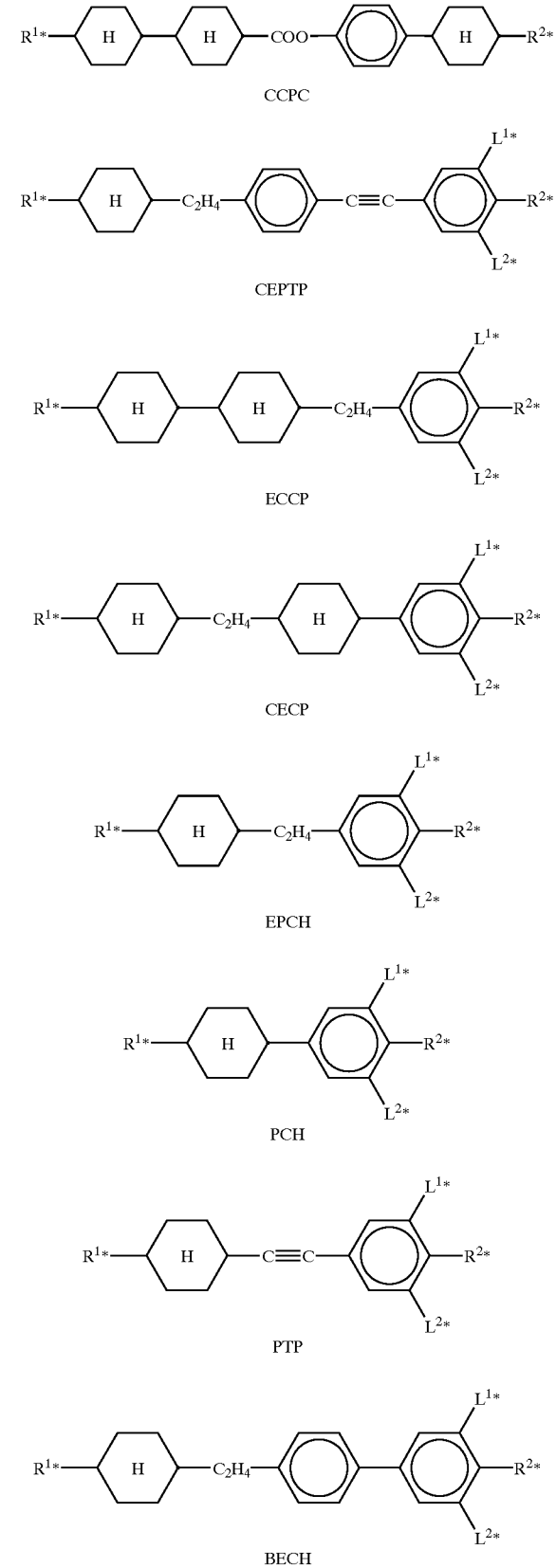

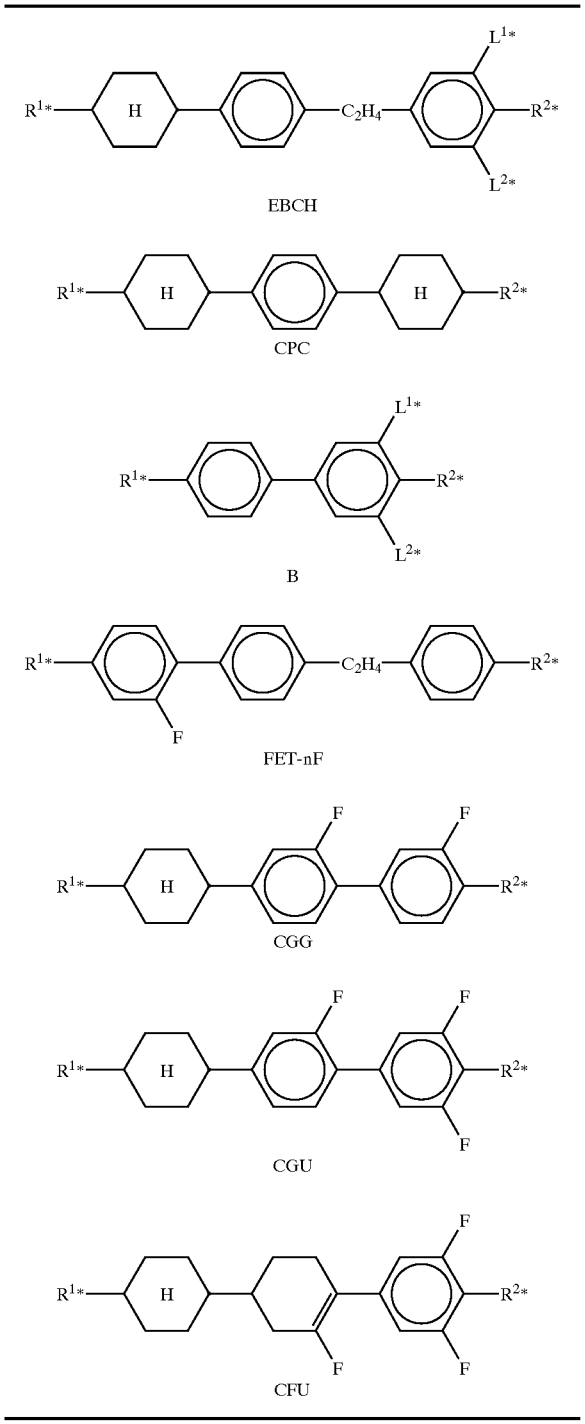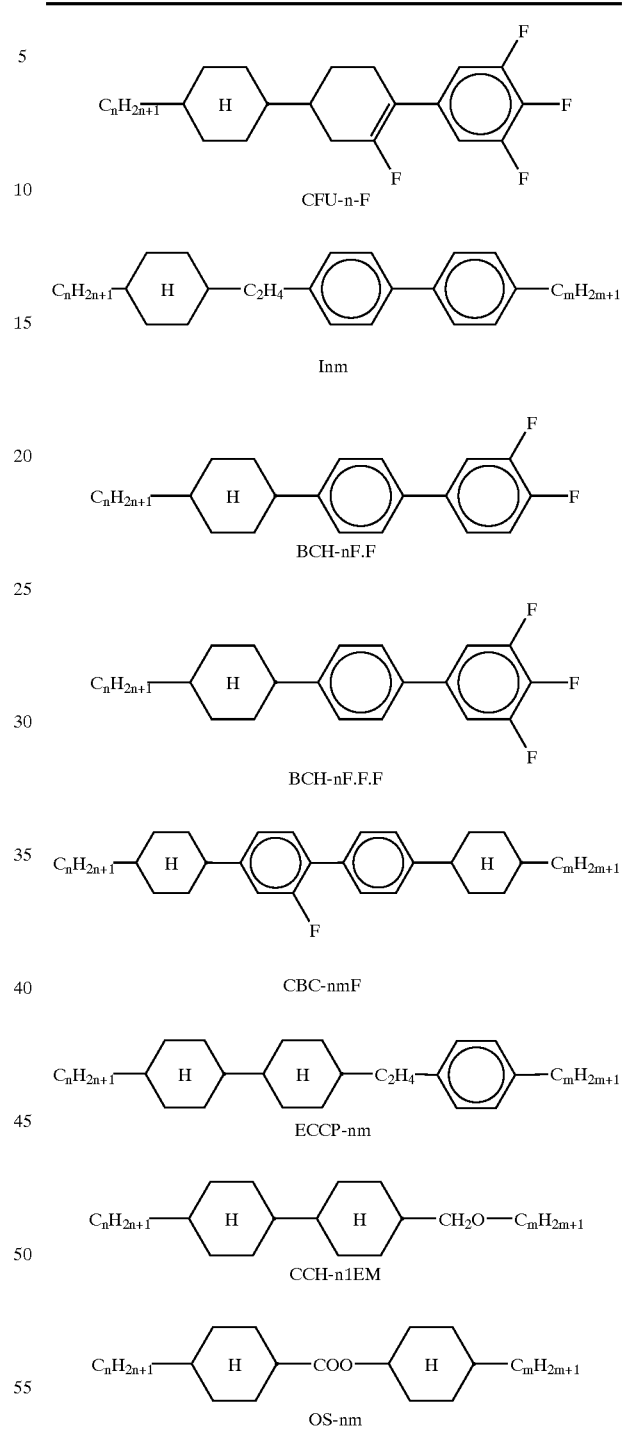

TABLE B-continued

CH-nm

CC-n-V

CGU-n-F

CDU-n-F

CGG-n-F

CDU-n-OD

CCP-nOCF₃

CCP-nOCF₂.F

CCP-nF.F.F

CCP-nOCF₃.F

CCQU-n-F

CQCU-n-F

Dec-U-n-F

GPTU-n-F

CZGU-n-F

CC-1V-V1

CC-n-V1

TABLE B-continued

CCTU-n-F

CECG-n-OT

CECU-n-OT

CCQPC-n-m

CCQP-n-SF5

TABLE C

Table C lists possible dopants which are usually added to the mixtures according to the invention.

C 15

CB 15

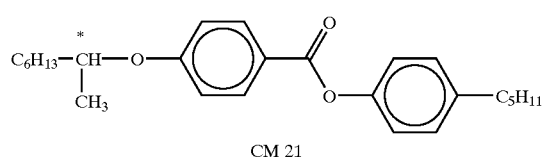

CM 21

TABLE C-continued

Table C lists possible dopants which are usually added to the mixtures according to the invention.

CM 33

R/S 811

CM 44

CM 45

CM 47

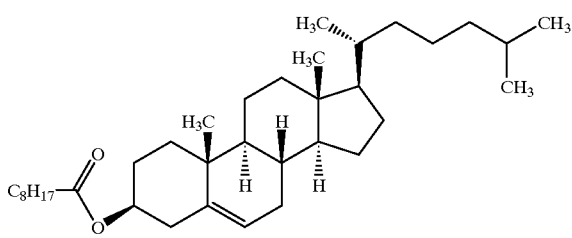

CN

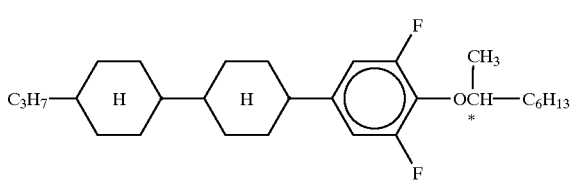

R/S 2011

Particular preference is given to mixtures according to the invention which comprise, in addition to one or more compounds of the formula I, two, three or more compounds selected from Table B.

The following examples are intended to illustrate the invention without limiting it. Hereinbefore and hereinafter, percentages are given in per cent by weight. All temperatures are specified in degrees Celsius. m.p. denotes melting point, cl.p.=clearing point. Furthermore, C=crystalline state, N=nematic phase, S=smectic phase and I=isotropic phase.

The data between these symbols represent the transition temperatures. Δn denotes the optical anisotropy (589 nm, 20° C.), and Δ∈ denotes the dielectric anisotropy (1 kHz, 20° C.). The flow viscosity $v_{20}$ (mm$^2$/sec) was determined at 20° C. The rotational viscosity $\gamma_1$ (mPa·s) was likewise determined at 20° C.

$V_{10}$ denotes the voltage for 10% transmission (viewing direction perpendicular to the plate surface). $t_{on}$ denotes the on time and $t_{off}$ the off time at an operating voltage corresponding to twice the value of $V_{10}$. Δn denotes the optical anisotropy and $n_o$ the refractive index. Δ∈ denotes the dielectric anisotropy (Δ∈=∈$_\|$−∈$_\perp$, where ∈$_\|$ is the dielectric constant parallel to the longitudinal axes of the molecule and ∈$_\perp$ is the dielectric constant perpendicular thereto). The electro-optical data were measured in a TN cell in the 1st minimum (i.e. at a d·Δn value of 0.5) at 20° C., unless expressly stated otherwise. The optical data were measured at 20° C., unless expressly stated otherwise.

"Conventional work-up" means that water is added if necessary, the mixture is extracted with methylene chloride, diethyl ether or toluene, the phases are separated, the organic phase is dried and evaporated, and the product is purified by distillation under reduced pressure or crystallization and/or chromatography.

The following abbreviations are used:
THF tetrahydrofuran
KOtBu potassium tert-butoxide
MTB ether methyl tert-butyl ether Example 1

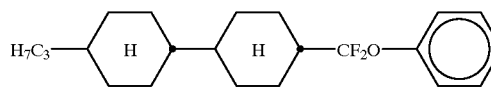

Step 1.1

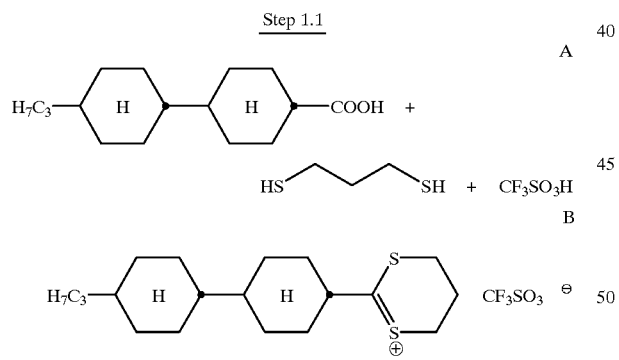

2.51 ml of trifluoromethanesulfonic acid are added to 0.998 mol of A and 0.998 mol of 1,3-propanedithiol with ice cooling. The resulting mixture is then stirred at 120° C. for 0.5 h. The mixture is allowed to cool, 300 ml of acetonitrile are added and the mixture is poured into 700 ml ice-cold diethyl ether. This suspension is cooled at −20° C. overnight, filtered off with suction under nitrogen, washed with diethyl ether and dried in vacuo.

Step 1.2

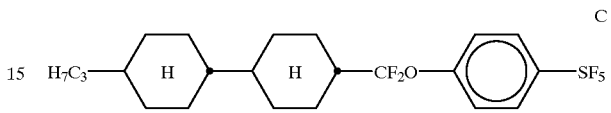

A mixture of 5 ml of triethylamine and 7.8 g of phenol in 10 ml of dichloromethane is added to 0.023 mol of triflate B in 110 ml of dichloromethane at −70° C. The mixture is stirred at −70° C. for 1.5 h, 0.036 mol of triethylamine hydrofluoride are added dropwise, and the resulting mixture is stirred for another 0.5 h. A solution of 0.117 mol of bromine in 10 ml of dichloromethane is then added dropwise at −70° C. The mixture is stirred at −70° C. for 1.5 h and allowed to warm to 0° C., saturated sodium bicarbonate solution is added and the mixture is subjected to conventional work-up. The product is recrystallized from n-heptane. C, 67; N, 116.5; I; Δ∈=12.0; Δn=0.0835.

The following compounds of the formula

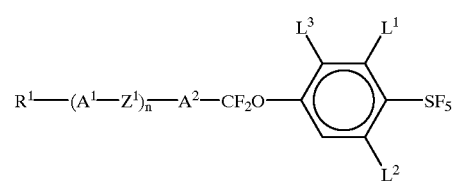

are prepared in a similar manner from the corresponding carboxylic acid:

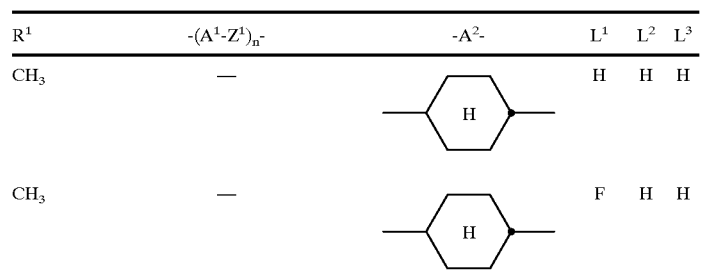

| $R^1$ | -($A^1$-$Z^1$)$_n$- | -$A^2$- | $L^1$ | $L^2$ | $L^3$ |
|---|---|---|---|---|---|
| CH$_3$ | — | (cyclohexyl) | H | H | H |
| CH$_3$ | — | (cyclohexyl) | F | H | H |

-continued
| R¹ | -(A¹-Z¹)ₙ- | -A²- | L¹ | L² | L³ |
|---|---|---|---|---|---|
| CH₃ | — | 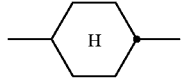 | F | F | H |
| CH₃ | — | 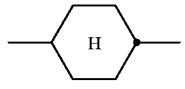 | F | H | F |
| C₂H₅ | — | 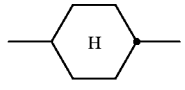 | H | H | H |
| C₂H₅ | — | 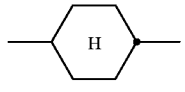 | F | H | H |
| C₂H₅ | — | 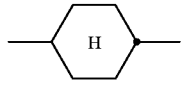 | F | F | H |
| C₂H₅ | — | 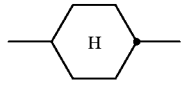 | F | H | F |
| n-C₃H₇ | — | 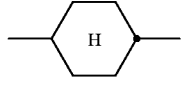 | H | H | H |
| n-C₃H₇ | — | 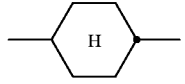 | F | H | H |
| n-C₃H₇ | — | 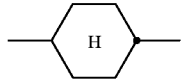 | F | F | H |
| n-C₃H₇ | — | 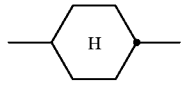 | F | H | F |
| n-C₄H₉ | — | 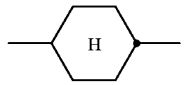 | H | H | H |
| n-C₄H₉ | — | 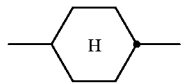 | F | H | H |
| n-C₄H₉ | — | 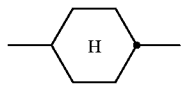 | F | F | H |

-continued
| R¹ | -(A¹-Z¹)ₙ- | -A²- | L¹ | L² | L³ |
|---|---|---|---|---|---|
| n-C₄H₉ | — | 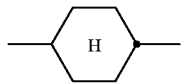 | F | H | F |
| n-C₅H₁₁ | — | 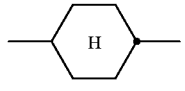 | H | H | H |
| n-C₅H₁₁ | — | 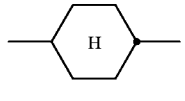 | F | H | H |
| n-C₅H₁₁ | — | 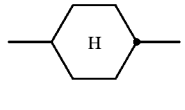 | F | F | H |
| n-C₅H₁₁ | — | 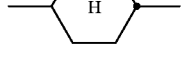 | F | H | F |
| CH₃ | — |  | H | H | H |
| CH₃ | — |  | F | H | H |
| CH₃ | — |  | F | F | H |
| CH₃ | — |  | F | H | F |
| C₂H₅ | — |  | H | H | H |
| C₂H₅ | — |  | F | H | H |
| C₂H₅ | — |  | F | F | H |
| C₂H₅ | — |  | F | H | F |
| n-C₃H₇ | — |  | H | H | H |

-continued
| R¹ | -(A¹-Z¹)ₙ- | -A²- | L¹ | L² | L³ |
|---|---|---|---|---|---|
| n-C₃H₇ | — |  | F | H | H |
| n-C₃H₇ | — |  | F | F | H |
| n-C₃H₇ | — |  | F | H | F |
| n-C₄H₉ | — |  | H | H | H |
| n-C₄H₉ | — |  | F | H | H |
| n-C₄H₉ | — |  | F | F | H |
| n-C₄H₉ | — |  | F | H | F |
| n-C₅H₁₁ | — |  | H | H | H |
| n-C₅H₁₁ | — |  | F | H | H |
| n-C₅H₁₁ | — |  | F | F | H |
| n-C₅H₁₁ | — |  | F | H | F |
| CH₃ | — | 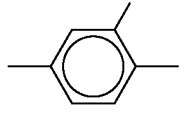 | H | H | H |
| CH₃ | — | 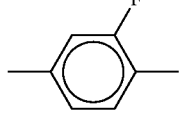 | F | H | H |

-continued
| R¹ | -(A¹-Z¹)ₙ- | -A²- | L¹ | L² | L³ |
|---|---|---|---|---|---|
| CH₃ | — | 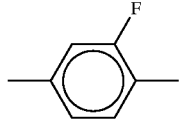 | F | F | H |
| CH₃ | — | 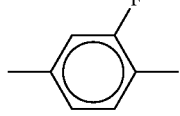 | F | H | F |
| C₂H₅ | — | 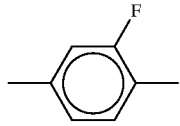 | H | H | H |
| C₂H₅ | — | 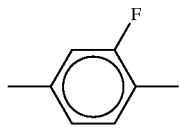 | F | H | H |
| C₂H₅ | — | 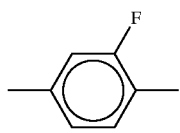 | F | F | H |
| C₂H₅ | — | 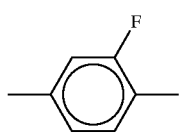 | F | H | F |
| n-C₃H₇ | — | 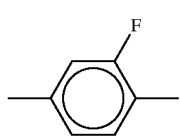 | H | H | H |
| n-C₃H₇ | — | 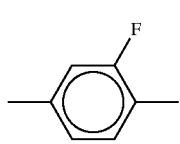 | F | H | H |
| n-C₃H₇ | — | 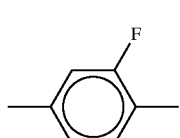 | F | F | H |
| n-C₃H₇ | — | 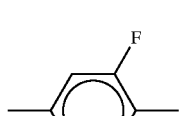 | F | H | F |
| n-C₄H₉ | — | 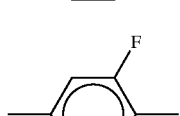 | H | H | H |

-continued
| R¹ | -(A¹-Z¹)ₙ- | -A²- | L¹ | L² | L³ |
|---|---|---|---|---|---|
| n-C₄H₉ | — | 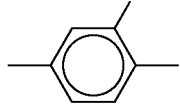 | F | H | H |
| n-C₄H₉ | — | 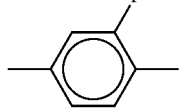 | F | F | H |
| n-C₄H₉ | — | 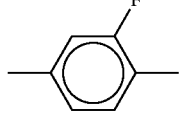 | F | H | F |
| n-C₅H₁₁ | — | 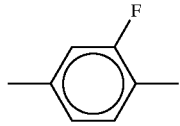 | H | H | H |
| n-C₅H₁₁ | — | 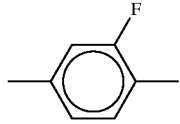 | F | H | H |
| n-C₅H₁₁ | — | 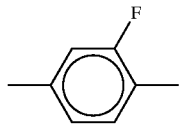 | F | F | H |
| n-C₅H₁₁ | — | 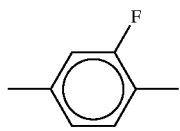 | F | H | F |
| CH₃ | — | 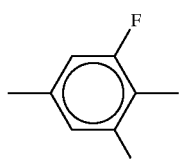 | H | H | H |
| CH₃ | — | 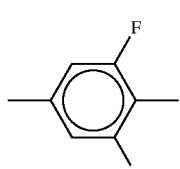 | F | H | H |
| CH₃ | — | 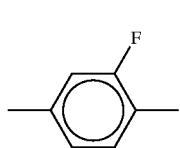 | F | F | H |

| R¹ | -(A¹-Z¹)ₙ- | -A²- | L¹ | L² | L³ |
|---|---|---|---|---|---|
| CH₃ | — | 3,5-difluorophenyl | F | H | F |
| C₂H₅ | — | 3,5-difluorophenyl | H | H | H |
| C₂H₅ | — | 3,5-difluorophenyl | F | H | H |
| C₂H₅ | — | 3,5-difluorophenyl | F | F | H |
| C₂H₅ | — | 3,5-difluorophenyl | F | H | F |
| n-C₃H₇ | — | 3,5-difluorophenyl | H | H | H |
| n-C₃H₇ | — | 3,5-difluorophenyl | F | H | H |
| n-C₃H₇ | — | 3,5-difluorophenyl | F | F | H |

-continued
| R¹ | -(A¹-Z¹)ₙ- | -A²- | L¹ | L² | L³ |
|---|---|---|---|---|---|
| n-C₃H₇ | — | 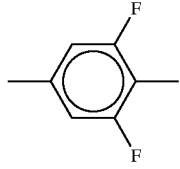 | F | H | F |
| n-C₄H₉ | — | 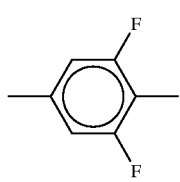 | H | H | H |
| n-C₄H₉ | — | 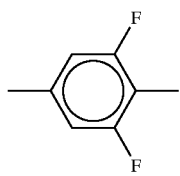 | F | H | H |
| n-C₄H₉ | — | 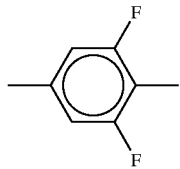 | F | F | H |
| n-C₄H₉ | — | 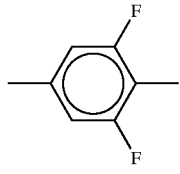 | F | H | F |
| n-C₅H₁₁ | — | 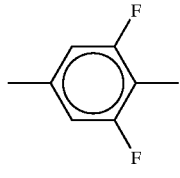 | H | H | H |
| n-C₅H₁₁ | — | 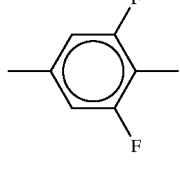 | F | H | H |
| n-C₅H₁₁ | — | 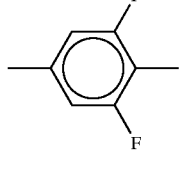 | F | F | H |

-continued
| R¹ | -(A¹-Z¹)ₙ- | -A²- | L¹ | L² | L³ |
|---|---|---|---|---|---|
| n-C₅H₁₁ | — | 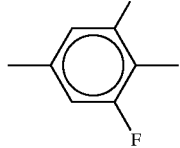 | F | H | F |
| CH₃ | 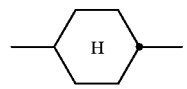 | 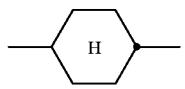 | H | H | H |
| CH₃ | 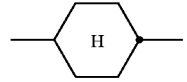 | 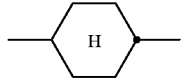 | F | H | H |
| CH₃ | 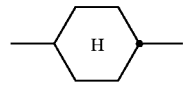 | 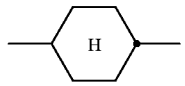 | F | F | H |
| CH₃ | 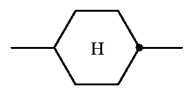 | 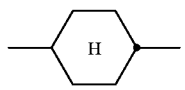 | F | H | F |
| C₂H₅ |  |  | H | H | H |
| C₂H₅ | 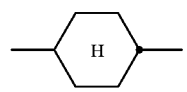 | 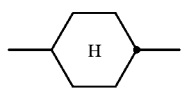 | F | H | H |
| C₂H₅ | 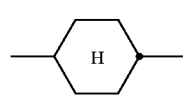 | 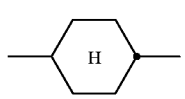 | F | F | H |
| C₂H₅ | 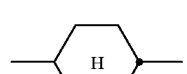 | 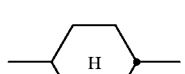 | F | H | F |
| n-C₃H₇ | 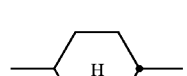 | 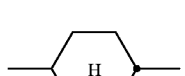 | F | H | H |
| n-C₃H₇ | 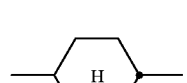 | 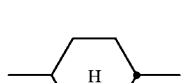 | F | F | H |
| n-C₃H₇ | 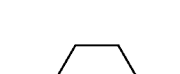 | 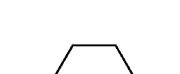 | F | H | F |
| n-C₅H₁₁ |  |  | H | H | H |

-continued

| R¹ | -(A¹-Z¹)ₙ- | -A²- | L¹ | L² | L³ |
|---|---|---|---|---|---|
| n-C₅H₁₁ | —Cy(H)— | —Cy(H)— | F | H | H |
| n-C₅H₁₁ | —Cy(H)— | —Cy(H)— | F | F | H |
| n-C₅H₁₁ | —Cy(H)— | —Cy(H)— | F | H | F |
| CH₃ | —Cy(H)—C₂F₄— | —Cy(H)— | H | H | H |
| CH₃ | —Cy(H)—C₂F₄— | —Cy(H)— | F | H | H |
| CH₃ | —Cy(H)—C₂F₄— | —Cy(H)— | F | F | H |
| CH₃ | —Cy(H)—C₂F₄— | —Cy(H)— | F | H | F |
| C₂H₅ | —Cy(H)—C₂F₄— | —Cy(H)— | H | H | H |
| C₂H₅ | —Cy(H)—C₂F₄— | —Cy(H)— | F | H | H |
| C₂H₅ | —Cy(H)—C₂F₄— | —Cy(H)— | F | F | H |
| C₂H₅ | —Cy(H)—C₂F₄— | —Cy(H)— | F | H | F |
| n-C₃H₇ | —Cy(H)—C₂F₄— | —Cy(H)— | H | H | H |
| n-C₃H₇ | —Cy(H)—C₂F₄— | —Cy(H)— | F | H | H |
| n-C₃H₇ | —Cy(H)—C₂F₄— | —Cy(H)— | F | F | H |

-continued

| R¹ | -(A¹-Z¹)ₙ- | -A²- | L¹ | L² | L³ |
|---|---|---|---|---|---|
| n-C₃H₇ | —⟨H⟩—C₂F₄— | —⟨H⟩— | F | H | F |
| n-C₅H₁₁ | —⟨H⟩—C₂F₄— | —⟨H⟩— | H | H | H |
| n-C₅H₁₁ | —⟨H⟩—C₂F₄— | —⟨H⟩— | F | H | H |
| n-C₅H₁₁ | —⟨H⟩—C₂F₄— | —⟨H⟩— | F | F | H |
| n-C₅H₁₁ | —⟨H⟩—C₂F₄— | —⟨H⟩— | F | H | F |
| CH₃ | —⟨H⟩— | —⟨F⟩— | H | H | H |
| CH₃ | —⟨H⟩— | —⟨F⟩— | F | H | H |
| CH₃ | —⟨H⟩— | —⟨F⟩— | F | F | H |
| CH₃ | —⟨H⟩— | —⟨F⟩— | F | H | F |
| C₂H₅ | —⟨H⟩— | —⟨F⟩— | H | H | H |
| C₂H₅ | —⟨H⟩— | —⟨F⟩— | F | H | H |
| C₂H₅ | —⟨H⟩— | —⟨F⟩— | F | F | H |

-continued

| R¹ | -(A¹-Z¹)ₙ- | -A²- | L¹ | L² | L³ |
|---|---|---|---|---|---|
| C₂H₅ | cyclohexyl | 3-F-phenyl | F | H | F |
| n-C₃H₇ | cyclohexyl | 3-F-phenyl | H | H | H |
| n-C₃H₇ | cyclohexyl | 3-F-phenyl | F | H | H |
| n-C₃H₇ | cyclohexyl | 3-F-phenyl | F | F | H |
| n-C₃H₇ | cyclohexyl | 3-F-phenyl | F | H | F |
| n-C₅H₁₁ | cyclohexyl | 3-F-phenyl | H | H | H |
| n-C₅H₁₁ | cyclohexyl | 3-F-phenyl | F | H | H |
| n-C₅H₁₁ | cyclohexyl | 3-F-phenyl | F | F | H |
| n-C₅H₁₁ | cyclohexyl | 3-F-phenyl | F | H | F |
| CH₃ | cyclohexyl | 3,5-di-F-phenyl | H | H | H |

-continued

| R¹ | -(A¹-Z¹)ₙ- | -A²- | L¹ | L² | L³ |
|---|---|---|---|---|---|
| CH₃ | cyclohexyl (H) | difluorophenyl (F,F) | F | H | H |
| CH₃ | cyclohexyl (H) | difluorophenyl (F,F) | F | F | H |
| CH₃ | cyclohexyl (H) | difluorophenyl (F,F) | F | H | F |
| C₂H₅ | cyclohexyl (H) | difluorophenyl (F,F) | H | H | H |
| C₂H₅ | cyclohexyl (H) | difluorophenyl (F,F) | F | H | H |
| C₂H₅ | cyclohexyl (H) | difluorophenyl (F,F) | F | F | H |
| C₂H₅ | cyclohexyl (H) | difluorophenyl (F,F) | F | H | F |
| n-C₃H₇ | cyclohexyl (H) | difluorophenyl (F,F) | H | H | H |

-continued

| R¹ | -(A¹-Z¹)ₙ- | -A²- | L¹ | L² | L³ |
|---|---|---|---|---|---|
| n-C₃H₇ | cyclohexyl | 3,5-difluorophenyl | F | H | H |
| n-C₃H₇ | cyclohexyl | 3,5-difluorophenyl | F | F | H |
| n-C₃H₇ | cyclohexyl | 3,5-difluorophenyl | F | H | F |
| n-C₅H₁₁ | cyclohexyl | 3,5-difluorophenyl | H | H | H |
| n-C₅H₁₁ | cyclohexyl | 3,5-difluorophenyl | F | H | H |
| n-C₅H₁₁ | cyclohexyl | 3,5-difluorophenyl | F | F | H |
| n-C₅H₁₁ | cyclohexyl | 3,5-difluorophenyl | F | H | F |
| CH₃ | cyclohexyl | 3-fluorophenyl | H | H | H |

-continued
| R¹ | -(A¹-Z¹)ₙ- | -A²- | L¹ | L² | L³ |
|---|---|---|---|---|---|
| CH₃ |  | 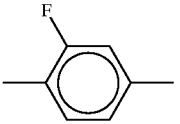 | F | H | H |
| CH₃ | 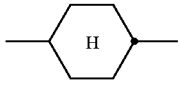 | 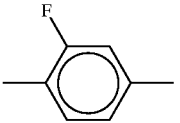 | F | F | H |
| CH₃ |  | 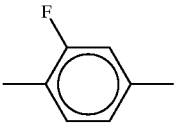 | F | H | F |
| C₂H₅ |  | 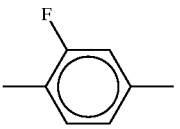 | H | H | H |
| C₂H₅ | 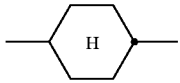 | 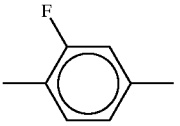 | F | H | H |
| C₂H₅ |  | 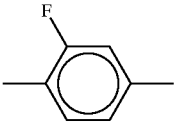 | F | F | H |
| C₂H₅ |  | 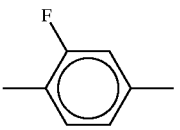 | F | H | F |
| n-C₃H₇ |  | 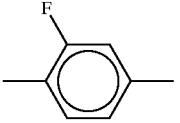 | H | H | H |
| n-C₃H₇ | 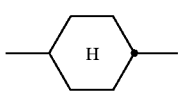 | 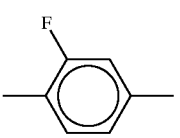 | F | H | H |
| n-C₃H₇ |  | 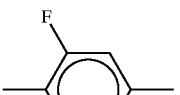 | F | F | H |
| n-C₃H₇ | 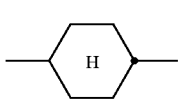 | 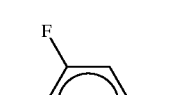 | F | H | F |

-continued

| R¹ | -(A¹-Z¹)ₙ- | -A²- | L¹ | L² | L³ |
|---|---|---|---|---|---|
| n-C₅H₁₁ | cyclohexyl | 2-F-phenyl | H | H | H |
| n-C₅H₁₁ | cyclohexyl | 2-F-phenyl | F | H | H |
| n-C₅H₁₁ | cyclohexyl | 2-F-phenyl | F | F | H |
| n-C₅H₁₁ | cyclohexyl | 2-F-phenyl | F | H | F |
| CH₃ | cyclohexyl | 2,3-diF-phenyl | H | H | H |
| CH₃ | cyclohexyl | 2,3-diF-phenyl | F | H | H |
| CH₃ | cyclohexyl | 2,3-diF-phenyl | F | F | H |
| CH₃ | cyclohexyl | 2,3-diF-phenyl | F | H | F |
| C₂H₅ | cyclohexyl | 2,3-diF-phenyl | H | H | H |
| C₂H₅ | cyclohexyl | 2,3-diF-phenyl | F | H | H |

-continued

| R¹ | -(A¹-Z¹)ₙ- | -A²- | L¹ | L² | L³ |
|---|---|---|---|---|---|
| C₂H₅ | cyclohexyl (trans) | 2,3-difluorophenyl | F | F | H |
| C₂H₅ | cyclohexyl (trans) | 2,3-difluorophenyl | F | H | F |
| n-C₃H₇ | cyclohexyl (trans) | 2,3-difluorophenyl | H | H | H |
| n-C₃H₇ | cyclohexyl (trans) | 2,3-difluorophenyl | F | H | H |
| n-C₃H₇ | cyclohexyl (trans) | 2,3-difluorophenyl | F | F | H |
| n-C₃H₇ | cyclohexyl (trans) | 2,3-difluorophenyl | F | H | F |
| n-C₅H₁₁ | cyclohexyl (trans) | 2,3-difluorophenyl | H | H | H |
| n-C₅H₁₁ | cyclohexyl (trans) | 2,3-difluorophenyl | F | H | H |
| n-C₅H₁₁ | cyclohexyl (trans) | 2,3-difluorophenyl | F | F | H |
| n-C₅H₁₁ | cyclohexyl (trans) | 2,3-difluorophenyl | F | H | F |

-continued

| R¹ | -(A¹-Z¹)ₙ- | -A²- | L¹ | L² | L³ |
|---|---|---|---|---|---|
| C₂H₅ | decahydronaphthalene | difluorophenyl | H | H | H |
| C₂H₅ | decahydronaphthalene | difluorophenyl | F | H | H |
| C₂H₅ | decahydronaphthalene | difluorophenyl | F | F | H |
| C₂H₅ | decahydronaphthalene | difluorophenyl | F | H | F |
| n-C₃H₇ | decahydronaphthalene | fluorophenyl | H | H | H |
| n-C₃H₇ | decahydronaphthalene | fluorophenyl | F | H | H |
| n-C₃H₇ | decahydronaphthalene | fluorophenyl | F | F | H |
| n-C₃H₇ | decahydronaphthalene | fluorophenyl | F | H | F |
| C₂H₁₁ | decahydronaphthalene | difluorophenyl | H | H | H |

-continued

| R¹ | -(A¹-Z¹)ₙ- | -A²- | L¹ | L² | L³ |
|---|---|---|---|---|---|
| C₂H₁₁ | [decalin] | [difluorobenzene] | F | H | H |
| C₂H₁₁ | [decalin] | [difluorobenzene] | F | F | H |
| C₂H₁₁ | [decalin] | [difluorobenzene] | F | H | F |
| n-C₃H₇ | [cyclohexyl-C₂F₄] | [phenyl] | H | H | H |
| n-C₃H₇ | [cyclohexyl-C₂F₄] | [phenyl] | F | H | H |
| n-C₃H₇ | [cyclohexyl-C₂F₄] | [phenyl] | F | F | H |
| n-C₃H₇ | [cyclohexyl-C₂F₄] | [phenyl] | F | H | F |
| n-C₃H₇ | [cyclohexyl-C₂F₄] | [fluorophenyl] | H | H | H |
| n-C₃H₇ | [cyclohexyl-C₂F₄] | [fluorophenyl] | F | H | H |
| n-C₃H₇ | [cyclohexyl-C₂F₄] | [fluorophenyl] | F | F | H |
| n-C₃H₇ | [cyclohexyl-C₂F₄] | [fluorophenyl] | F | H | F |

-continued

| R¹ | -(A¹-Z¹)ₙ- | -A²- | L¹ | L² | L³ |
|---|---|---|---|---|---|
| n-C₃H₇ | cyclohexyl-C₂F₄- | 2,6-difluorophenyl | H | H | H |
| n-C₃H₇ | cyclohexyl-C₂F₄- | 2,6-difluorophenyl | F | H | H |
| n-C₃H₇ | cyclohexyl-C₂F₄- | 2,6-difluorophenyl | F | F | H |
| n-C₃H₇ | cyclohexyl-C₂F₄- | 2,6-difluorophenyl | F | H | F |
| n-C₅H₁₁ | cyclohexyl-C₂F₄- | phenyl | H | H | H |
| n-C₅H₁₁ | cyclohexyl-C₂F₄- | phenyl | F | H | H |
| n-C₅H₁₁ | cyclohexyl-C₂F₄- | phenyl | F | F | H |
| n-C₅H₁₁ | cyclohexyl-C₂F₄- | phenyl | F | H | F |
| n-C₃H₇ | cyclohexyl-C₂F₄- | 2-fluorophenyl | H | H | H |
| n-C₅H₁₁ | cyclohexyl-C₂F₄- | 2-fluorophenyl | F | H | H |

-continued

| R¹ | -(A¹-Z¹)ₙ- | -A²- | L¹ | L² | L³ |
|---|---|---|---|---|---|
| n-C₅H₁₁ | Cyclohexyl-C₂F₄- | difluorophenyl | F | F | H |
| n-C₅H₁₁ | Cyclohexyl-C₂F₄- | difluorophenyl | F | H | F |
| n-C₅H₁₁ | Cyclohexyl-C₂F₄- | trifluorophenyl | H | H | H |
| n-C₅H₁₁ | Cyclohexyl-C₂F₄- | trifluorophenyl | F | H | H |
| n-C₅H₁₁ | Cyclohexyl-C₂F₄- | trifluorophenyl | F | F | H |
| n-C₅H₁₁ | Cyclohexyl-C₂F₄- | trifluorophenyl | F | H | F |

Example M1

| | | | |
|---|---|---|---|
| BCH-3F.F | 10.8% | Clearing point: | 93.8° C. |
| BCH-5F.F | 9.0% | Δn [589 nm; 20° C.]: | +0.095 |
| ECCP-30CF₃ | 4.5% | Δε [1 kHz; 20° C.]: | 5.9 |
| ECCP-50CF₃ | 4.5% | | |
| CBC-33F | 1.8% | | |
| CBC-53F | 1.8% | | |
| CBC-55F | 1.8% | | |
| PCH-6F | 7.2% | | |
| PCH-7F | 5.4% | | |
| CCP-20CF₃ | 7.2% | | |
| CCP-30CF₃ | 10.8% | | |
| CCP-40CF₃ | 6.3% | | |
| CCP-50CF₃ | 9.9% | | |
| PCH-5F | 9.0% | | |
| CCQP-3-SF₅ | 10.0% | | |

Example M2

| | | | |
|---|---|---|---|
| PCH-5F | 3.20% | Clearing point: | 123.8° C. |
| CCP-20CF₂.F.F | 17.04% | Δε [1 kHz; 20° C.]: | 9.1 |
| CCP-30CF₂.F.F | 16.00% | | |
| CCP-50CF₂.F.F | 17.04% | | |
| CUP-2F.F | 5.36% | | |
| CUP-3F.F | 5.36% | | |
| CBC-33F | 5.36% | | |
| CBC-53F | 5.36% | | |
| CBC-55F | 5.28% | | |
| CCQP-3-SF₅ | 20.00% | | |

Example M3

| | | | |
|---|---|---|---|
| BCH-3F.F | 10.74% | γ₁ [mPa · s; 20° C.]: | 154 |
| BCH-5F.F | 8.95% | | |
| ECCP-30CF₃ | 4.48% | | |

| | |
|---|---|
| ECCP-50CF₃ | 4.48% |
| CBC-33F | 1.79% |
| CBC-53F | 1.79% |
| CBC-55F | 1.79% |
| PCH-6F | 7.16% |
| PCH-7F | 5.37% |
| CCP-20CF₃ | 7.16% |
| CCP-30CF₃ | 10.74% |
| CCP-40CF₃ | 6.27% |
| CCP-50CF₃ | 9.85% |
| PCH-5F | 8.95% |
| CCQP-3-SF₅ | 10.50% |

The preceding examples can be repeated with similar success by substituting the generically or specifically described reactants and/or operating conditions of this invention for those used in the preceding examples. Also, the preceding specific embodiments are to be construed as merely illustrative, and not limitative of the remainder of the disclosure in any way whatsoever.

What is claimed is:

1. A pentafluorosulfuranylbenzene compound of the formula I

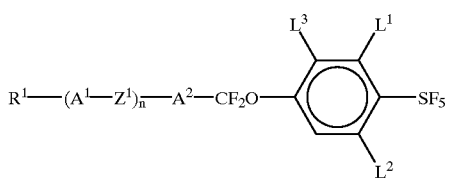

in which $R^1$ is H or an alkyl or alkylene radical having 1 to 15 carbon atoms which is unsubstituted or monosubstituted by CN or $CF_3$, or monosubstituted to perhalosubstituted by halogen and in which, one or more non-adjacent $CH_2$ groups are optionally each independently of one another, replaced by —O—, —C≡C—, —S—, —CO—,

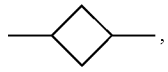

—CO—O—, —O—CO— or —O—CO—O— in such a way that oxygen atoms are not linked directly to one another, $A^1$ and $A^2$ are, independently of one another,
 a) a trans-cyclohexane-1,4-diyl radical, in which, in addition, one or more non-adjacent $CH_2$ groups are optionally replaced by —O— and/or —S—,
 b) a 1,4-phenylene radical, in which, in addition, one or two CH groups are optionally replaced by N,
 c) a radical selected from the group consisting of 1,4-bicyclo[2.2.2]-octylene, piperidine-1,4-diyl, naphthalene-2,6-diyl, decahydronaphthalene-2,6-diyl and 1,2,3,4-tetrahydronaphthalene-2,6-diyl,
 d) a cyclohexylene-1,4-diyl radical, where the radicals a), b), c) and d) are optionally substituted by CN, $CH_3$, Cl or F, $L^1$, $L^2$, $L^3$ are H, CN, F or Cl, $Z^1$ is —CO—O—, —O—CO—, —CH₂O—, —O—, —OCH₂—, —CH₂CH₂—, —CHFCH₂—, —CH═CH—, —CH₂CF₂—, —CF₂CH₂—, —CF₂CHF—, —CHFCF₂—, —C≡C—, —C₂F₄—, —CF═CF—, —OCF₂—, —CF₂O— or a single bond, and n is 0, 1, 2 or 3.

2. A pentafluorosulfuranylbenzene compound of claim 1, wherein $L^1$ or $L^2$ is fluorine or wherein $L^1$ and $L^2$ are fluorine.

3. A pentafluorosulfuranylbenzene compound of claim 1, wherein $L^1$ or $L^3$ is fluorine or wherein $L^1$ and $L^3$ are fluorine.

4. A pentafluorosulfuranylbenzene compound of claim 1, wherein $R^1$ is straight-chain alkyl or alkoxy having 1 to 10 carbon atoms or alkenyl or alkenyloxy having 2 to 10 carbon atoms.

5. A pentafluorosulfuranylbenzene compound of claim 1, wherein $Z^1$ is —CH₂CH₂—, —CH═CH—, —C≡C—, —CF₂CF₂—, —CF═CF—, —CF₂O—, —OCF₂— or a single bond.

6. A pentafluorosulfuranylbenzene compound of claim 1, wherein n is 0 or 1.

7. A pentafluorosulfuranylbenzene compound of claim 1, in which $A^1$ is trans-cyclohexane-1,4-diyl or 1,4-phenylene which is unsubstituted or substituted by one or two fluorine atoms.

8. A liquid-crystalline medium comprising at least one compound of the formula I of claim 1 and another liquid-crystalline component.

9. A liquid-crystal display element, which comprises a liquid-crystalline medium according to claim 8.

10. An electro-optical display element, which comprises as dielectric, a liquid-crystalline medium according to claim 8.

11. A pentafluorosulfuranylbenzene compound of claim 1, said compound being of formulae Ia, Ib or Ic $R^1\text{-}A^2\text{-}CF_2O\text{-}A^3\text{-}SF_5$  Ia, $R^1\text{-}A^1\text{-}A^2\text{-}CF_2O\text{-}A^3\text{-}SF_5$  Ib, $R^1A^1\text{-}Z^1A^2\text{-}CF_2O\text{-}A^3\text{-}SF_5$  Ic, wherein $A^3$ is

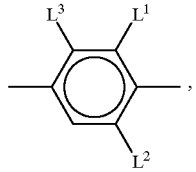

and $R^1$, $A^1$, $A^2$, $A^3$, $L^1$, $L^2$, $L^3$ and $Z^1$ are as defined in claim 1.

12. A pentafluorosulfuranylbenzene compound of claim 1, wherein n is 2.

13. A pentafluorosulfuranylbenzene compound of claim 1, wherein $A^1$ is a 1,4-phenylene radical, a 1,3-dioxane-2,5-diyl radical, or a 1,4-cyclohexylene radical.

14. A pentafluorosulfuranylbenzene compound of claim 1, wherein $A^1$ is trans-cyclohexane-1,4-diyl or 1,4-phenylene.

15. A pentafluorosulfuranylbenzene compound of claim 1, wherein $A^1$ or $A^2$ are 1,4-phenylene which is mono- or disubstituted by F or CN.

16. A pentafluorosulfuranylbenzene compound of claim 1, wherein $A^2$ is

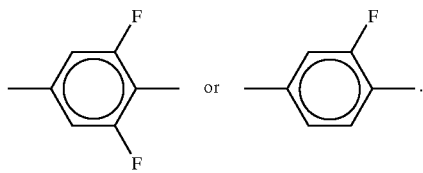

17. A pentafluorosulfuranylbenzene compound of claim 1, wherein $A^1$ is

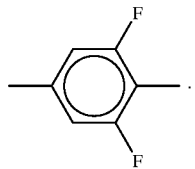

18. A pentafluorosulfuranylbenzene compound of claim 1, wherein $R^1$ is straight chain alkyl or alkoxy having 1 to 10 carbon atoms or alkenyl having 2 to 10 carbon atoms and Z is —CF$_2$CF$_2$— or —CF=CF—.

19. A pentafluorosulfuranylbenzene compound of claim 17, wherein wherein $R^1$ is straight-chain alkyl or alkoxy having 1 to 10 carbon atoms or alkenyl or alkenyloxy having 2 to 10 carbon atoms.

20. A pentafluorosulfuranylbenzene compound of claim 1, wherein $A^1$ and $A^2$ are, independently,

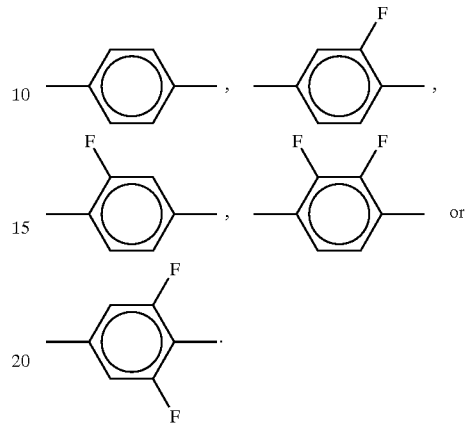

* * * * *